US011820539B2

(12) United States Patent
Feith et al.

(10) Patent No.: US 11,820,539 B2
(45) Date of Patent: *Nov. 21, 2023

(54) MANIFOLD FOR AUTOMATIC DRUG COMPOUNDER

(71) Applicant: CareFusion 303, Inc., San Diego, CA (US)

(72) Inventors: Ray P. Feith, San Diego, CA (US); Vincent Fuji Wang, San Diego, CA (US); Neil Quitoviera, Murrieta, CA (US); George Michael Mansour, Pomona, CA (US); Christopher J. Zollinger, Chino Hills, CA (US); Matthew Quach, San Gabriel, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/980,401

(22) Filed: Nov. 3, 2022

(65) Prior Publication Data

US 2023/0065197 A1    Mar. 2, 2023

Related U.S. Application Data

(60) Continuation of application No. 17/172,913, filed on Feb. 10, 2021, now Pat. No. 11,530,055, which is a (Continued)

(51) Int. Cl.
*B65B 3/00* (2006.01)
*B65B 3/12* (2006.01)
(Continued)

(52) U.S. Cl.
CPC ............... *B65B 3/003* (2013.01); *A61J 1/10* (2013.01); *A61J 1/201* (2015.05); *A61J 1/2075* (2015.05);
(Continued)

(58) Field of Classification Search
CPC ......... B65B 3/003; A61J 1/201; A61J 1/2075; A61J 3/002

See application file for complete search history.

(56) References Cited

U.S. PATENT DOCUMENTS 4,031,688 A    6/1977   Wasserman
4,373,559 A    2/1983   Mowles
(Continued)

FOREIGN PATENT DOCUMENTS

CN    201127755 Y    10/2008
CN    103462803 A    12/2013
(Continued)

OTHER PUBLICATIONS

Chinese Office Action for Application No. 201680079734.0, dated Apr. 13, 2020, 17 pages.
(Continued)

*Primary Examiner* — Timothy L Maust
(74) *Attorney, Agent, or Firm* — Morgan, Lewis & Bockius LLP

(57) ABSTRACT

A manifold for control of fluid and/or vapor flow between a container and a pump cartridge for a compounder system is provided. One or more manifolds may be disposed in a magazine configured to secure and align the manifolds with a plurality of ports in the cartridge. Each manifold may include a needle having forward and rear openings to a central bore. A needle housing may include a slot configured to receive a push rod for actuating the needle forward and backward. In a forward, engaged position, the openings in the needle may be disposed on opposite sides of a sealing member of the manifold to form a fluid pathway through the manifold. In a rearward, disengaged position, both the forward and rear openings in the needle may be disposed on
(Continued)

the same side of the sealing member to prevent fluid and vapor from flowing through the manifold.

20 Claims, 39 Drawing Sheets

Related U.S. Application Data division of application No. 15/780,609, filed as application No. PCT/US2016/064021 on Nov. 29, 2016, now Pat. No. 10,954,007.

(60) Provisional application No. 62/263,562, filed on Dec. 4, 2015.

(51) Int. Cl.
*A61J 3/00* (2006.01)
*A61J 1/20* (2006.01)
*A61J 1/10* (2006.01)
*A61M 39/10* (2006.01)

(52) U.S. Cl.
CPC ............... *A61J 3/002* (2013.01); *B65B 3/12* (2013.01); *A61M 39/10* (2013.01)

(56) References Cited

U.S. PATENT DOCUMENTS

| | | |
|---|---|---|
| 4,576,211 A | 3/1986 | Valentini |
| 5,062,774 A | 11/1991 | Kramer et al. |
| 5,526,853 A | 6/1996 | McPhee |
| 5,957,166 A | 9/1999 | Safabash |
| 6,572,823 B1 | 6/2003 | Donahue et al. |
| 6,689,108 B2 | 2/2004 | Lavi et al. |
| 7,703,486 B2 | 4/2010 | Costanzo |
| 8,287,513 B2 | 10/2012 | Ellstrom |
| 8,540,691 B2 | 9/2013 | Hasegawa |
| 10,772,799 B2 | 9/2020 | Schneider et al. |
| 10,772,800 B2 | 9/2020 | Zollinger et al. |
| 10,925,808 B2 | 2/2021 | Pak et al. |
| 10,954,007 B2 | 3/2021 | Feith et al. |
| 11,185,472 B2 | 11/2021 | Oda et al. |
| 11,234,900 B2 | 2/2022 | Oda et al. |
| 11,530,055 B2 * | 12/2022 | Feith .................. B65B 3/12 |
| 2001/0025671 A1 | 10/2001 | Safabash |
| 2002/0007671 A1 | 1/2002 | Lavi et al. |
| 2002/0104584 A1 | 8/2002 | Spero |
| 2007/0038189 A1 | 2/2007 | Bartholomew |
| 2008/0277021 A1 | 11/2008 | Horppu |
| 2010/0108681 A1 | 5/2010 | Jepson et al. |
| 2015/0057613 A1 | 2/2015 | Clemente et al. |
| 2015/0257974 A1 | 9/2015 | Demers et al. |
| 2016/0310362 A1 | 10/2016 | Lane et al. |

FOREIGN PATENT DOCUMENTS

| | | |
|---|---|---|
| CN | 107278158 A | 9/2015 |
| EP | 1128858 A1 | 5/2001 |
| JP | S60222059 A | 11/1985 |
| JP | H07163665 A | 6/1995 |
| JP | 2007054186 A | 3/2007 |
| JP | 2009513267 A | 4/2009 |
| JP | 2010274443 A | 12/2010 |
| JP | 2013240647 A | 12/2013 |

OTHER PUBLICATIONS

Chinese Office Action for Application No. 201680079734.0, dated Aug. 28, 2020, 7 pages.
International Search Report and Written Opinion for Application No. PCT/US2016/064021, dated Mar. 23, 2017, 8 pages.
Japanese Office Action for Application No. 2018-529056, dated Jan. 22, 2021, 5 pages including translation.
Japanese Office Action for Application No. 2018-529056, dated Sep. 29, 2020, 14 pages.
Israel Office Action for Application No. 259581, dated Mar. 16, 2021, 8 pages including translation.
Japanese Office Action for Application No. 2021-085828, dated Mar. 8, 2022, 4 pages including translation.

* cited by examiner

MANIFOLD FOR AUTOMATIC DRUG COMPOUNDER

REFERENCE TO RELATED APPLICATIONS

This application is a continuation of U.S. patent application Ser. No. 17/172,913, filed on Feb. 10, 2021, issued as U.S. Pat. No. 11,530,055, on Dec. 20, 2022, which is a divisional of U.S. patent application Ser. No. 15/780,609, filed on May 31, 2018, issued as U.S. Pat. No. 10,954,007, on Mar. 23, 2021, which is the National Stage Entry of PCT/US2016/064021, filed on Nov. 29, 2016, and claims priority to U.S. Provisional Patent Application No. 62/263,562, filed Dec. 4, 2015, the entire disclosure of each of these applications being incorporated herein by this reference.

TECHNICAL FIELD

The present disclosure generally relates to an apparatus that reconstitutes, mixes, and delivers a drug from a vial to a receiving container. Specifically, the present disclosure relates to a disposable magazine and manifold providing closed system diluent and waste paths for reconstitution of a drug, delivery of diluents from hung diluent bags and diluent vials to medication vials, filling of a receiving container, and removal of waste to a waste container.

BACKGROUND

Pharmaceutical compounding is the practice of creating a specific pharmaceutical product to fit the unique need of a patient. In practice, compounding is typically performed by a pharmacist, tech or a nurse who combines the appropriate ingredients using various tools. One common form of compounding comprises the combination of a powdered drug formulation with a specific diluent to create a suspended pharmaceutical composition. These types of compositions are commonly used in intravenous/parenteral medications. It is vital that the pharmaceuticals and diluents are maintained in a sterile state during the compounding process, and there exists a need for automating the process while maintaining the proper mixing characteristics (i.e., certain pharmaceuticals must be agitated in specific ways so that the pharmaceutical is properly mixed into solution but the solution is not frothed and air bubbles are not created). There exists a need for a compounding system that is easy to use, may be used frequently and efficiently, is reliable and reduces user error.

SUMMARY

One or more embodiments of a compounder system, include a pump head assembly having a recess and a plurality of operational mechanisms; a magazine configured to be received in the recess; a manifold configured to be received in the magazine; a container fluidly coupled to the manifold; and a pump cartridge configured to be operated by the plurality of operational mechanisms of the pump drive to pump a fluid from the container through the manifold into the pump cartridge, wherein the manifold comprises a needle assembly having a disengaged configuration in which the needle assembly is completely disposed within the manifold such that the manifold prevents flow of the fluid and an engaged configuration in which a needle of the needle assembly extends from the manifold into the pump cartridge such that the needle forms a portion of a sealed fluid pathway from the container to the pump cartridge.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The present system comprises multiple features and technologies that in conjunction form a compounding system that can efficiently reconstitute pharmaceuticals in a sterile environment and deliver the compounded pharmaceutical to a delivery bag for use on a patient.

Figure 1:
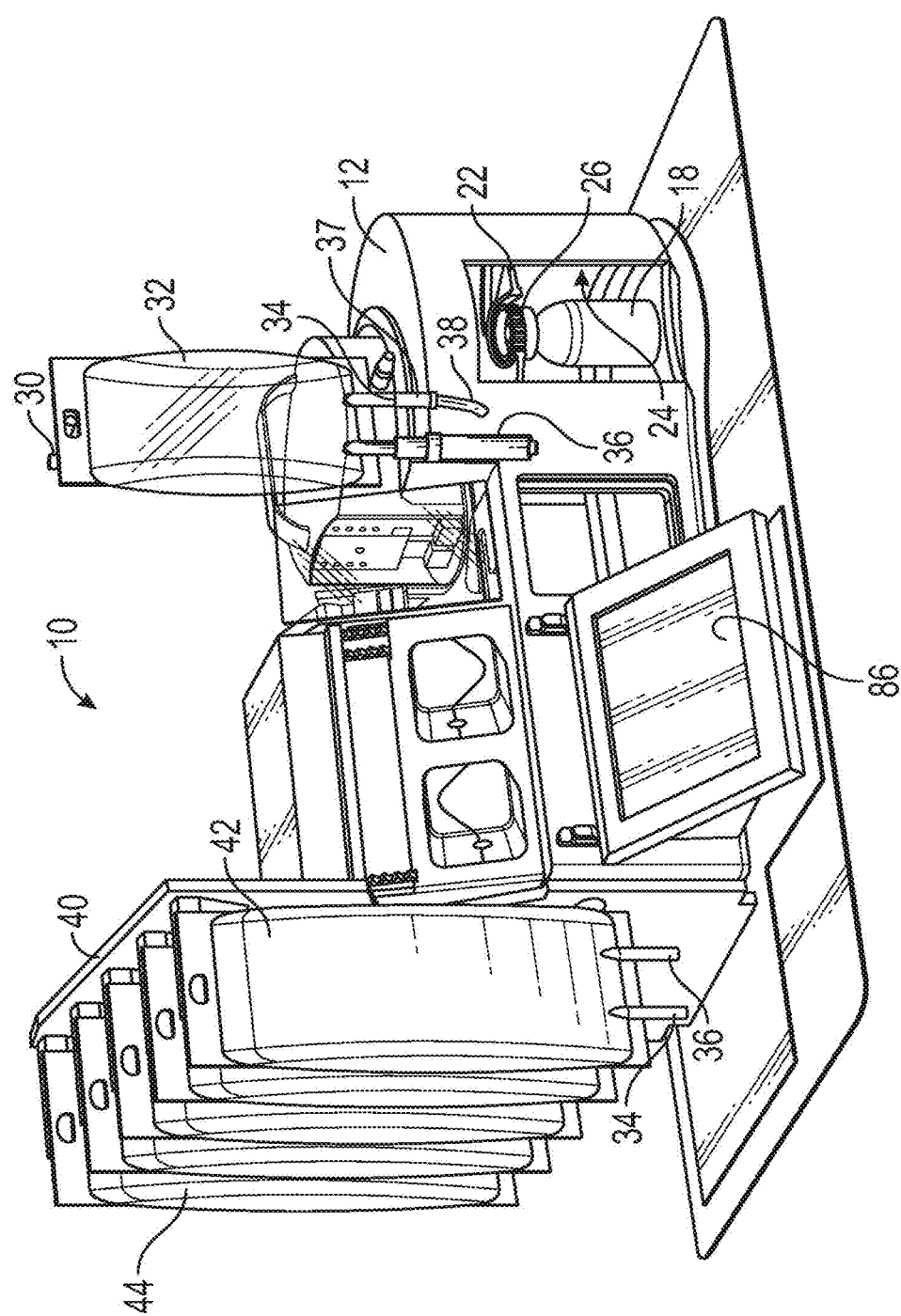
FIG. 1 illustrates a front perspective view of an example of an exemplary embodiment of a compounding system in accordance with aspects of the present disclosure.
Figure 2:
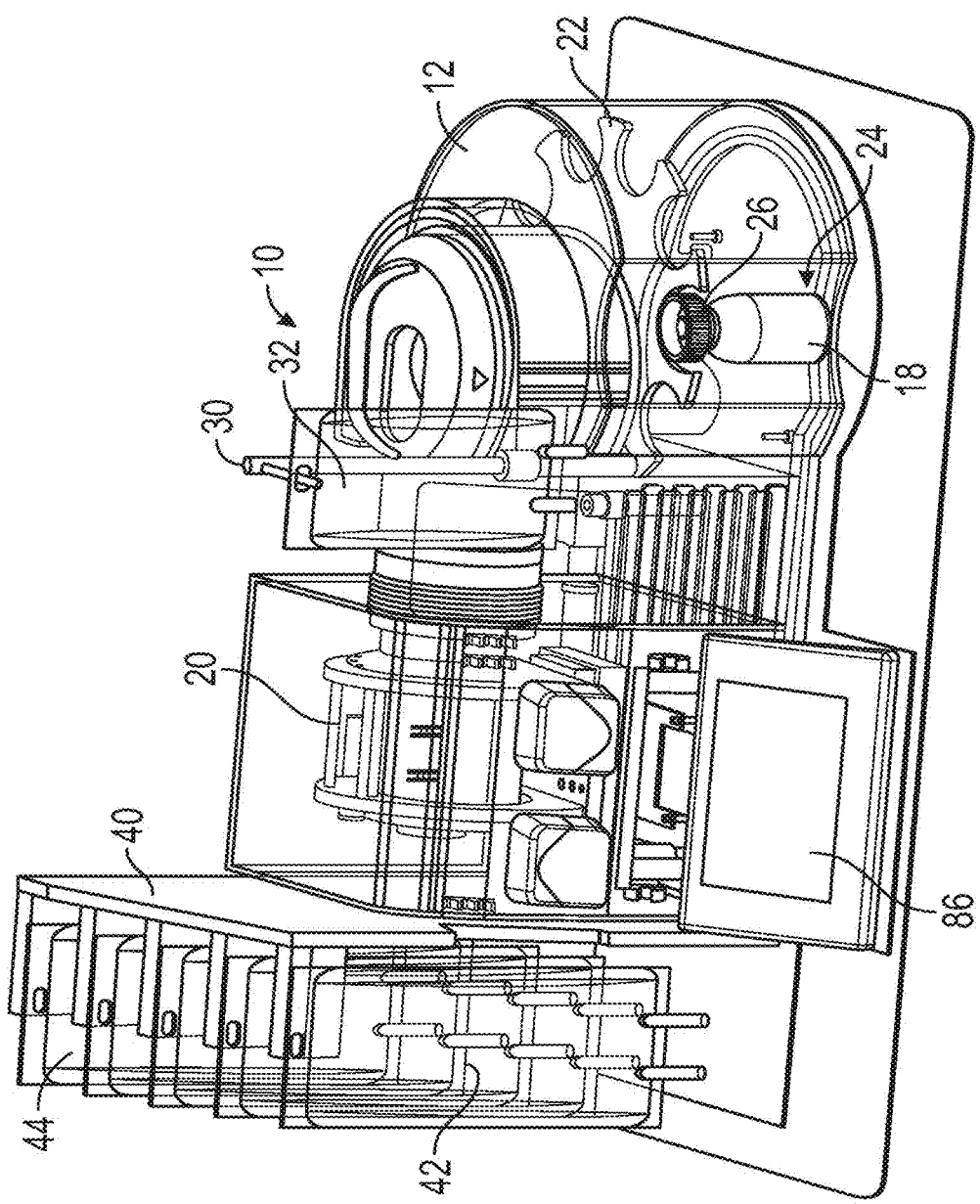
FIG. 2 illustrates a front perspective view of the compounding system of FIG. 1 with a transparent housing in accordance with aspects of the present disclosure.
Figure 3:
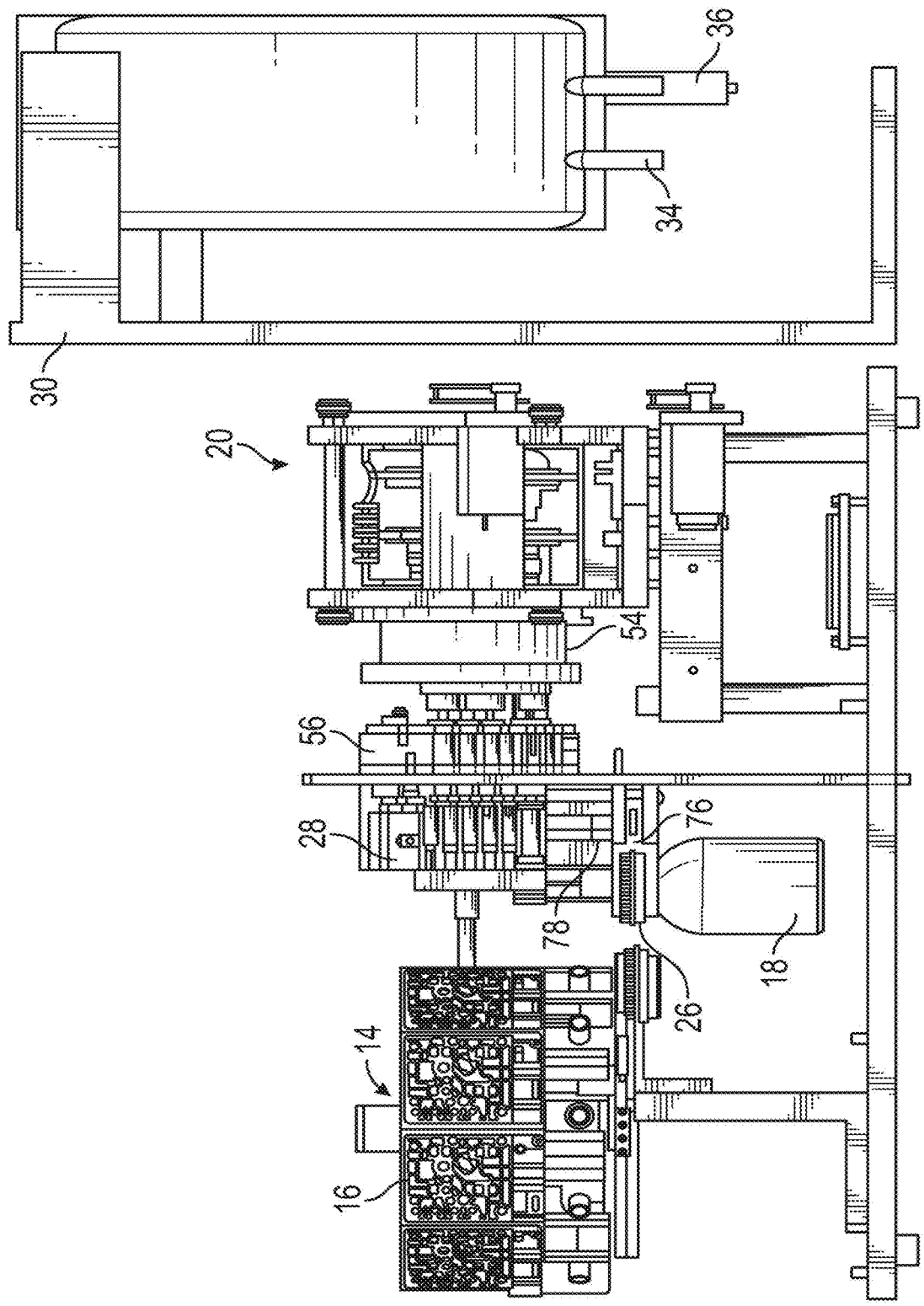
FIG. 3 illustrates a side view of the compounding system of FIG. 1 with the housing removed in accordance with aspects of the present disclosure.

FIG. 1 illustrates a compounder system 10 according to an embodiment. FIG. 2 illustrates the system 10 with a transparent outer housing 12 and FIG. 3 illustrates the system with the housing removed. The system comprises a carousel assembly 14 that contains up to 10 individual cartridges 16. The carousel 14 can hold more or less cartridges 16 if desired. The cartridges 16 are disposable and provide unique fluid paths between a vial 18 containing a powdered drug (or concentrated liquid drug), multiple diluents, and a receiving container. The cartridges 16 may, if desired, also provide a fluid path to a vapor waste container. However, in other embodiments, filtered or unfiltered non-toxic waste may be vented from the compounder to the environment reducing or eliminating the need for a waste port. Each cartridge contains a piston pump and valves that control the fluid intake, outtake, and fluid path selection during the steps of the compounding process as the fluid moves through the cartridge and into a receiving container.

The carousel assembly 14 is mounted on the apparatus such that it can rotate to bring different cartridges 16 into alignment with the pump drive mechanism 20. The carousel 14 is typically enclosed within a housing 12 that can be opened in order to replace the carousel 14 with a new carousel 14 after removing a used one. As illustrated, the carousel 14 can contain up to 10 cartridges 16, allowing a particular carousel to be used up to 10 times. In this configuration, each carousel assembly can support, for example, 10 to 100 receiving containers, depending on the type of compounding to be performed. For example, for hazardous drug compounding, a carousel assembly can support compounding to ten receiving containers. In another example, for non-hazardous drug compounding such as antibiotic or pain medication compounding, a carousel assembly can support compounding to 100 receiving containers. The housing 12 also includes a star wheel 22 positioned underneath the carousel 14. The star wheel 22 rotates vials 18 of pharmaceuticals into position either in concert with, or separate from, the specific cartridges 16 on the carousel 14. The housing 12 may also include an opening 24 for loading the vials 18 into position on the star wheel 22.

Each one of the cartridges 16 in the carousel 14 is a disposable unit that includes multiple pathways for the diluent and vapor waste. Each cartridge 16 is a small, single disposable unit that may also include a "backpack" in which a tube for connection to the receiving container (e.g., an IV bag, a syringe, or an elastomeric bag) may be maintained. Each cartridge 16 also includes a piston pump for moving fluid and vapor through the cartridge 16 as well as a duel lumen needle in a housing that can pierce a vial puck 26 on top of a vial 18 once the vial 18 has been moved into position by the pump drive mechanism 20. For example, the needle may pierce the vial puck 26 via the compressive action of the vial puck 26, which is moved towards the needle. Each cartridge 16 also includes a plurality of ports designed to match up with the needles of a plurality of diluent manifolds. Each cartridge 16 also includes openings to receive mounting posts and a locking bayonet from the pump head assembly 28. Although a locking bayonet is described herein as an example, other locking mechanisms may be used to retrieve and lock a cartridge to the pump head (e.g., grippers, clamps, or the like may extend from the pump head). Each cartridge 16 also includes openings allowing valve actuators from the pump motor mechanism to interact with the valves on each cartridge 16.

Adjacent the housing 12 that holds the vials 18 and the carousel 14 is an apparatus 30 for holding at least one container 32, such as an IV bag 32 as shown in the figures. The IV bag 32 typically has two ports such as ports 34 and 36. For example, in one implementation, port 34 is an intake port 34 and port 36 is an outlet port 36. The IV bag 32 hangs from the holding apparatus 30, which, in one embodiment is a post with a hook as illustrated in FIGS. 1-3. One or more of the hooks for hanging containers such as diluent containers, receiving containers, or waste containers may be provided with a weight sensor such as a load cell that detects and monitors the weight of a hung container. The holding apparatus 30 can take any other form necessary to position the IV bag 32 or other pharmaceutical container. Once the IV bag 32 is positioned on the holding apparatus 30, a first tube 38 (a portion of which is shown in FIG. 1) is connected from a cartridge 16 on the carousel 14 to the inlet 34 of the IV bag 32. For example, the first tube may be housed in a backpack attached to the cartridge and extended from within the backpack (e.g., by an operator or automatically) to reach the IV bag 32. A connector 37 such as a Texium® connector may be provided on the end of tube 38 for connecting to inlet 34 of receiving container 32.

On the opposite side of the compounder 10 is an array of holding apparatuses 40 for holding multiple IV bags 32 or other containers. In the illustrated version of the compounder 10, five IV bags 42, 44 are pictured. Three of these bags 42 may contain diluents, such as saline, D5 W or sterile water, although any diluent known in the art may be utilized. An additional bag in the array may be an empty vapor waste bag 44 for collecting waste such as potentially hazardous or toxic vapor waste from the mixing process. An additional bag 44 may be a liquid waste bag. The liquid waste bag may be configured to receive non-toxic liquid waste such as saline from a receiving container. Liquid waste may be pumped to the waste bag via dedicated tubing using a mechanical pump. In operation, diluent lines and a vapor waste line from the corresponding containers 42 and 44 may each be connected to a cartridge 16 through a disposable manifold.

The compounding system 10 also includes a specialized vial puck 26 designed to attach to multiple types of vials 18. In operation, the vial puck 26 is placed on top of the vial 18 containing the drug in need of reconstitution. Once the vial puck 26 is in place, the vial 18 is loaded into the star wheel 22 of the compounder 10. Mating features on the vial puck 26 provide proper alignment both while the vial puck 26 is in the star wheel 22 and when the vial puck 26 is later rotated into position so that the compounder 10 can remove it from the star wheel 22 for further processing.

Figure 4:
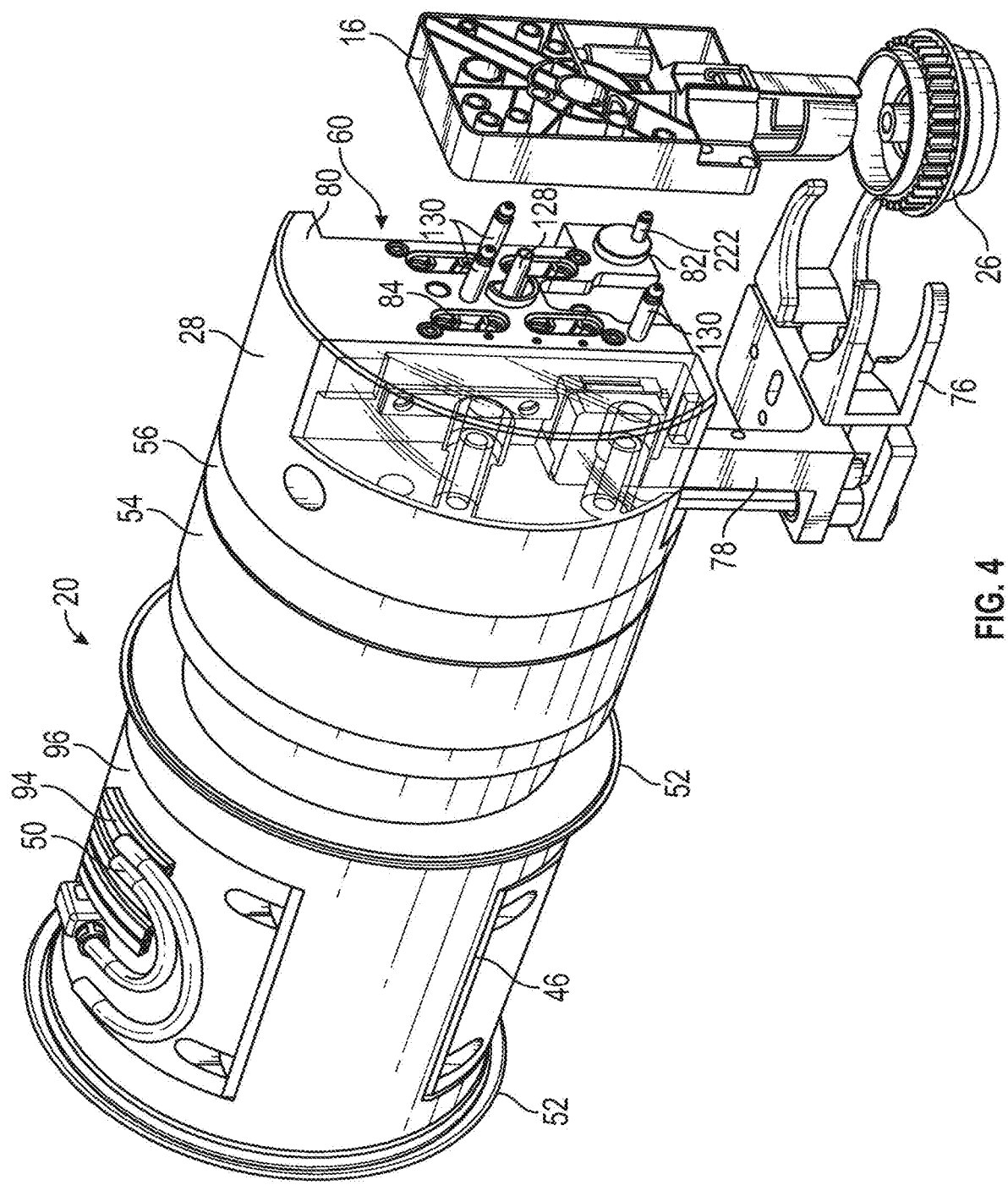
FIG. 4 illustrates a perspective view of an exemplary embodiment of a pump drive mechanism in accordance with aspects of the present disclosure.
Figure 5:
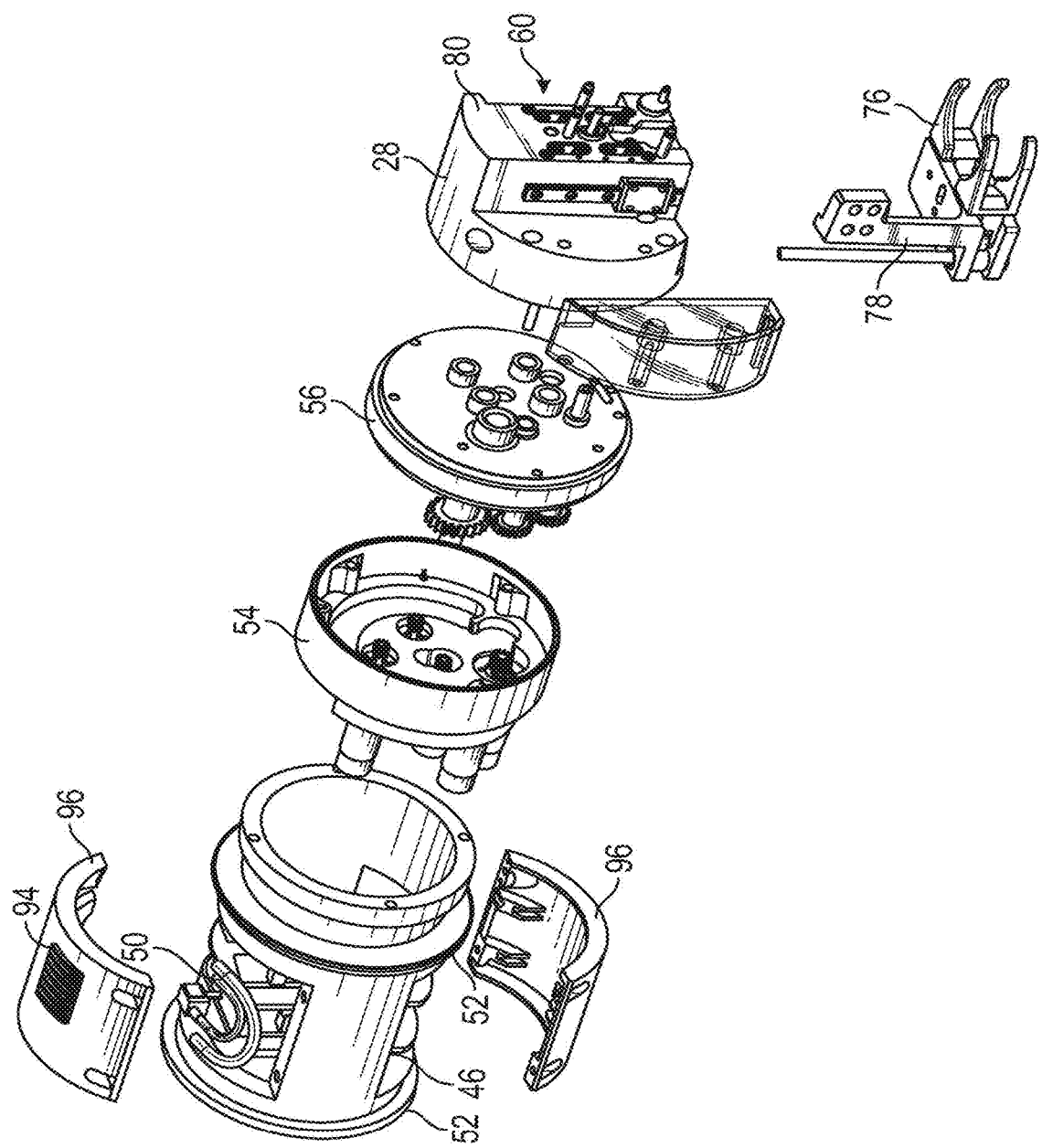
FIG. 5 illustrates an exploded view of the pump drive mechanism of FIG. 4 in accordance with aspects of the present disclosure.

The pump drive mechanism 20 is illustrated in FIG. 4, and in an exploded view in FIG. 5, according to an embodiment. In the embodiment shown in FIGS. 4 and 5, the pump drive mechanism 20 comprises a multitude of sections. At one end of the pump drive mechanism 20 is the rotation housing 46, which holds the drive electronics and includes locking flanges 94 on its housing 96 for flexible tubing 50 which may run from one or more diluent containers and/or waste containers to one or more corresponding manifolds. The rotation housing 46 is capable of rotating around its axis to rotate the rest of the pump drive mechanism 20. The rotation housing 46 includes bearing ribs 52 on its ends which allow it to rotate. For example, the pump drive mechanism may be configured to rotate through any suitable angle such as up to and including 180.degree., or more than 180.degree.

Figure 6:
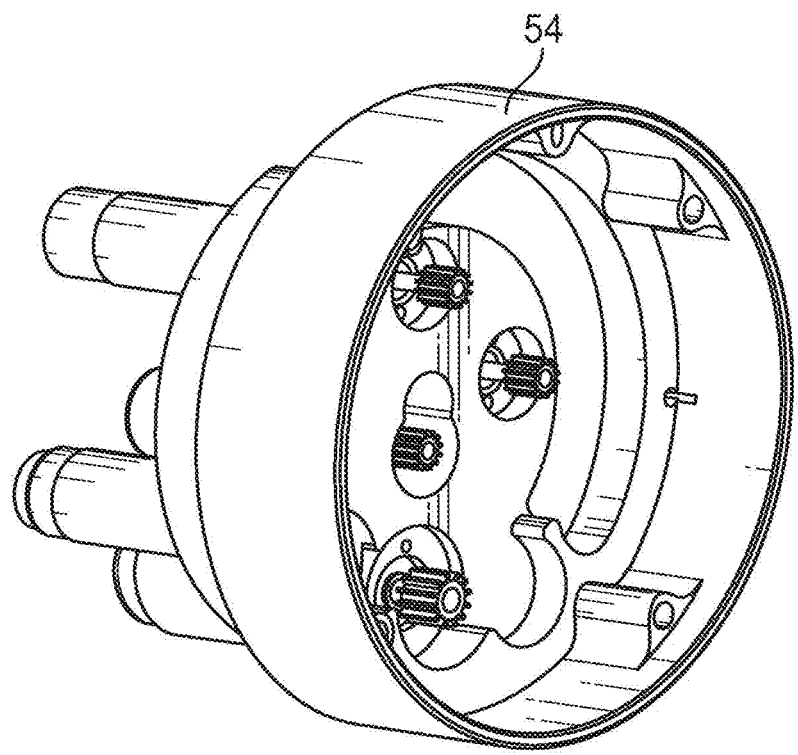
FIG. 6 illustrates a perspective view of an example of an exemplary embodiment of a motor mount in accordance with aspects of the present disclosure.
Figure 7:
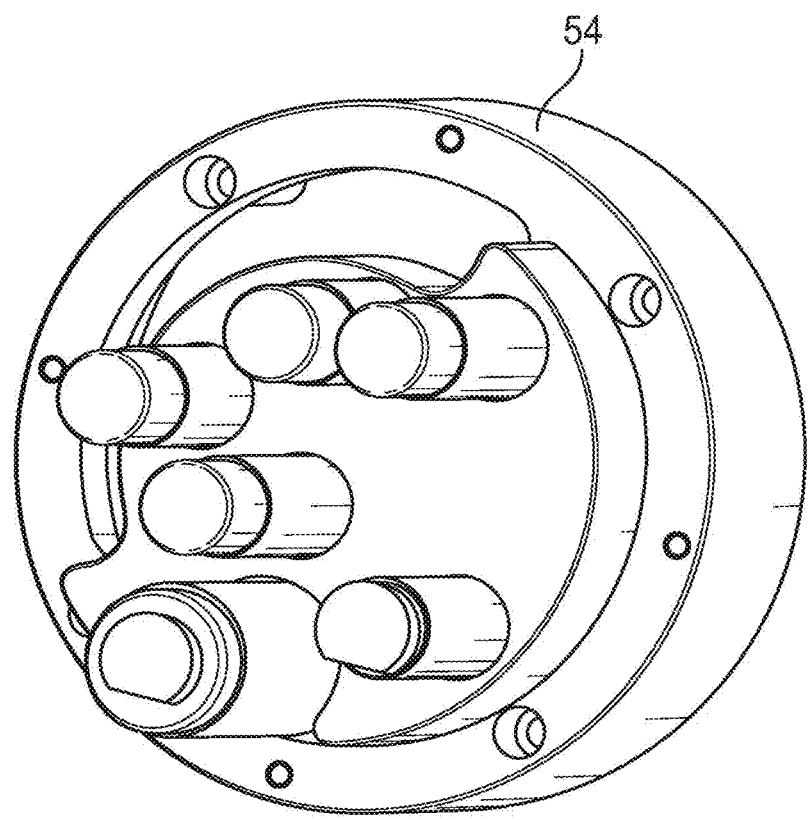
FIG. 7 illustrates a rear perspective view of the motor mount of FIG. 6 in accordance with aspects of the present disclosure.
Figure 8:
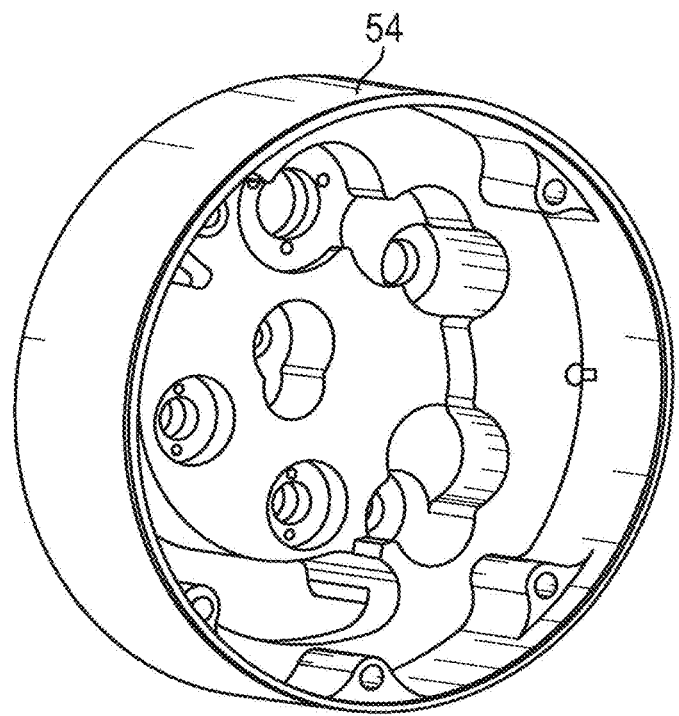
FIG. 8 illustrates a perspective view of the motor mount of FIG. 6 in accordance with aspects of the present disclosure.
Figure 9:
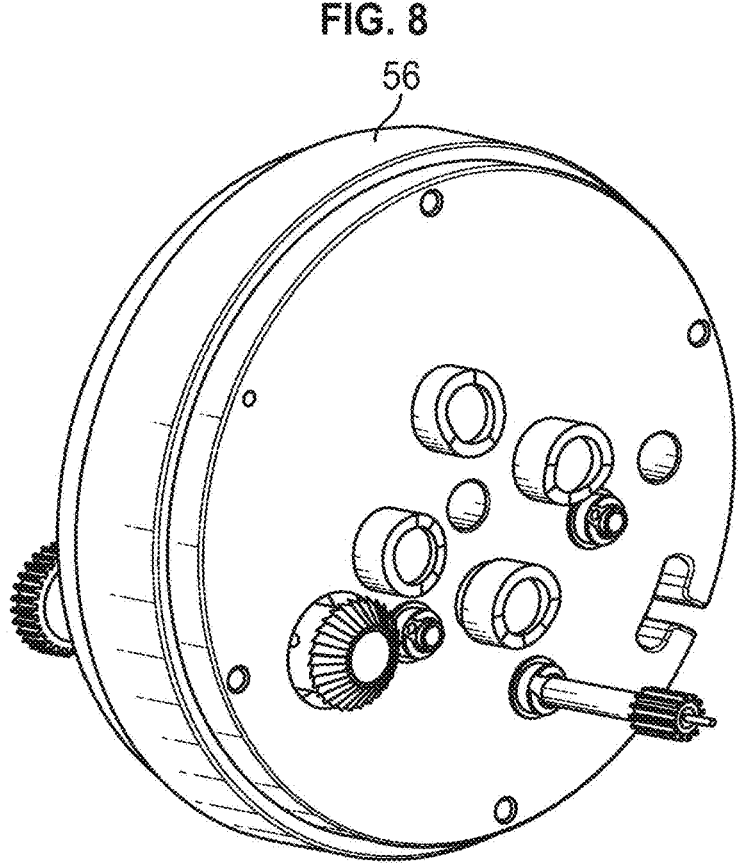
FIG. 9 illustrates a perspective view of an exemplary embodiment of a cam housing in accordance with aspects of the present disclosure.
Figure 10:
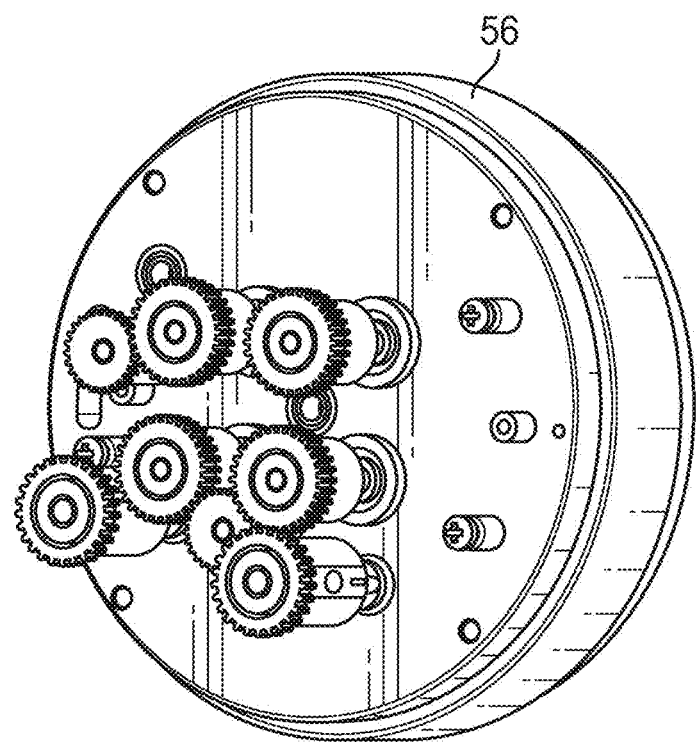
FIG. 10 illustrates a rear perspective view of the cam housing of FIG. 9 in accordance with aspects of the present disclosure.
Figure 11:
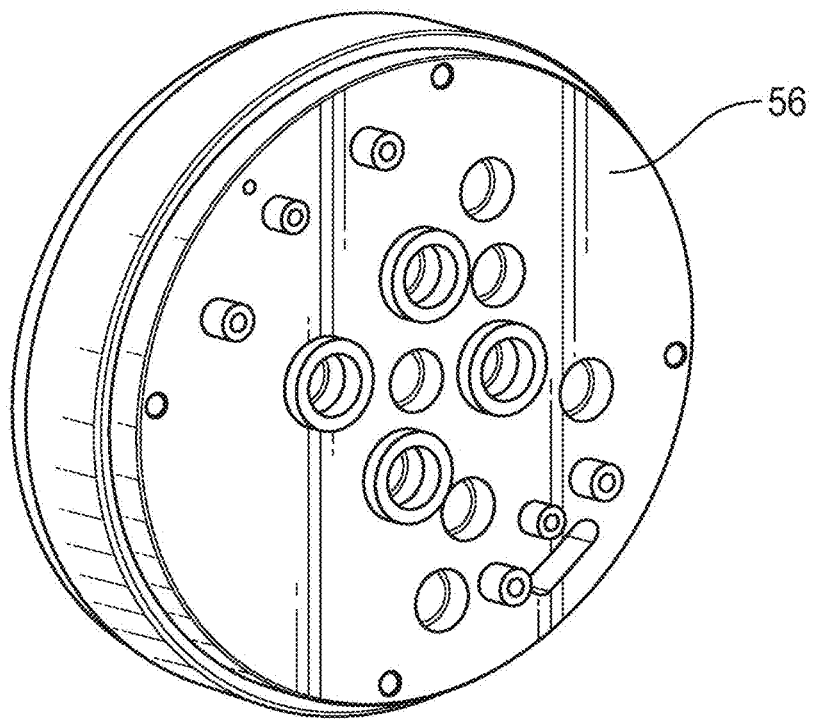
FIG. 11 illustrates a rear perspective view of the cam housing of FIG. 9 with the gears removed in accordance with aspects of the present disclosure.
Figure 12:
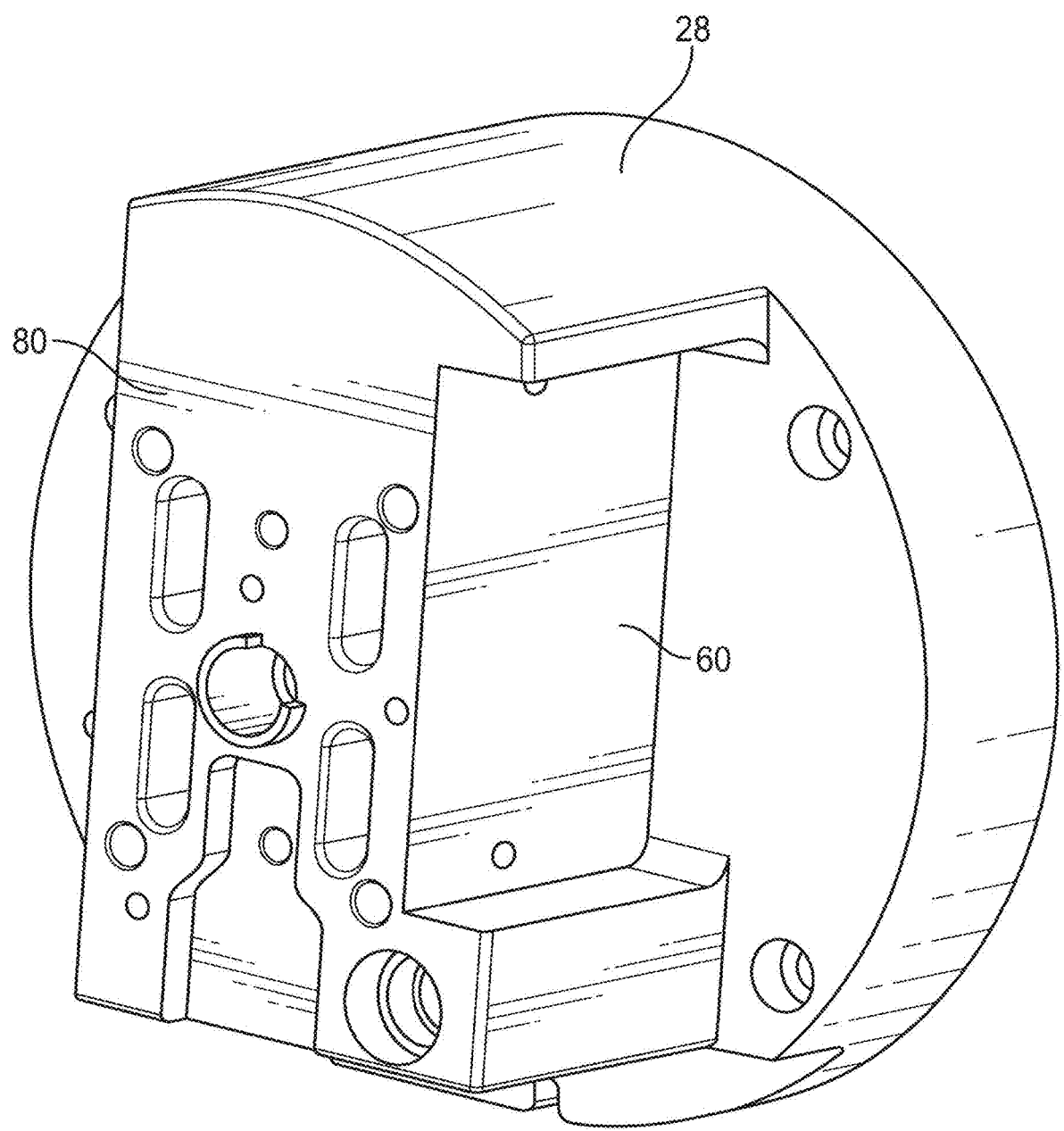
FIG. 12 illustrates a perspective view of an exemplary embodiment of a pump head assembly in accordance with aspects of the present disclosure.
Figure 13:
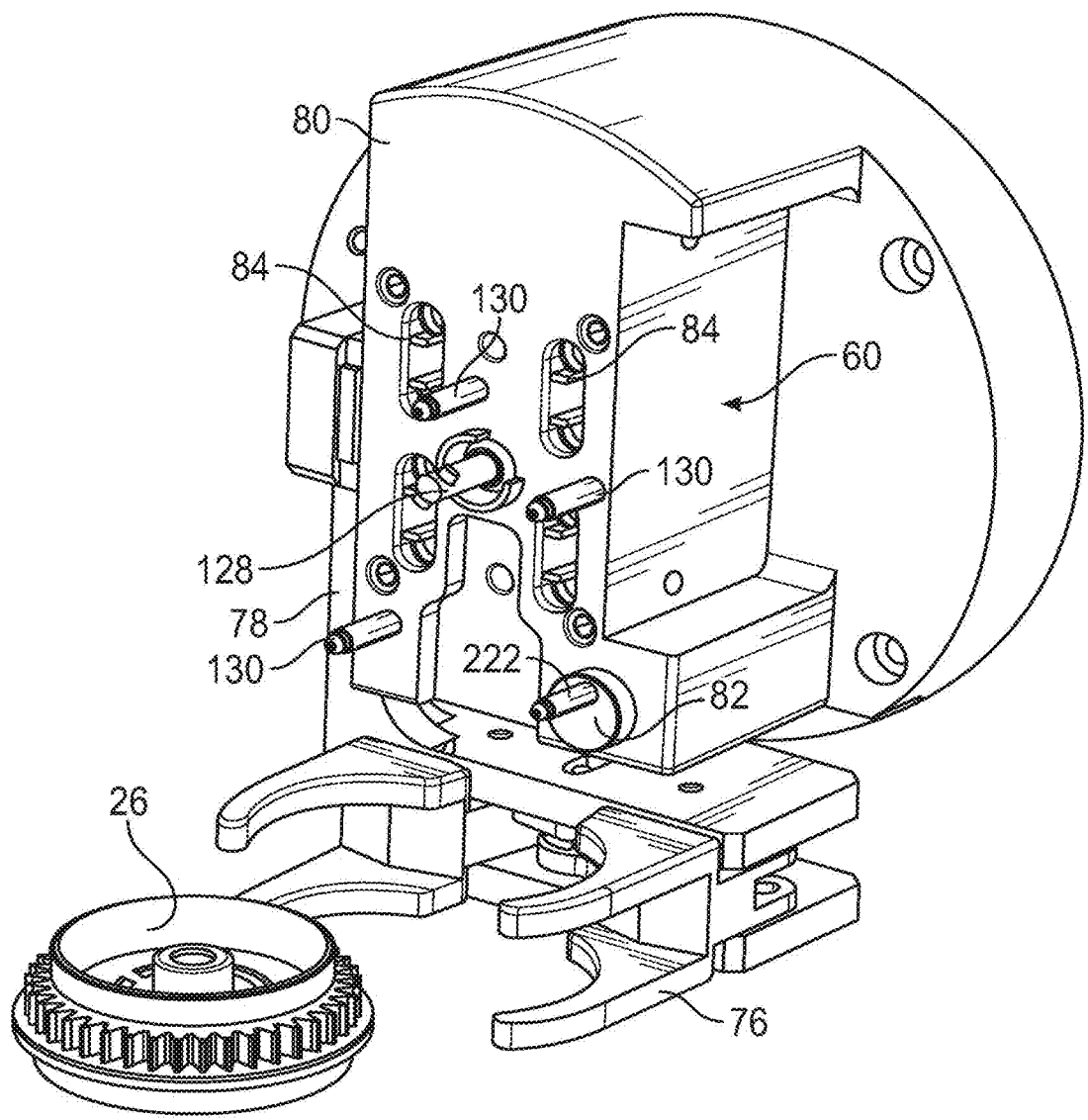
FIG. 13 illustrates a perspective view of the pump head assembly of FIG. 12 with an exemplary embodiment of a gripping system and vial puck in accordance with aspects of the present disclosure.
Figure 14:
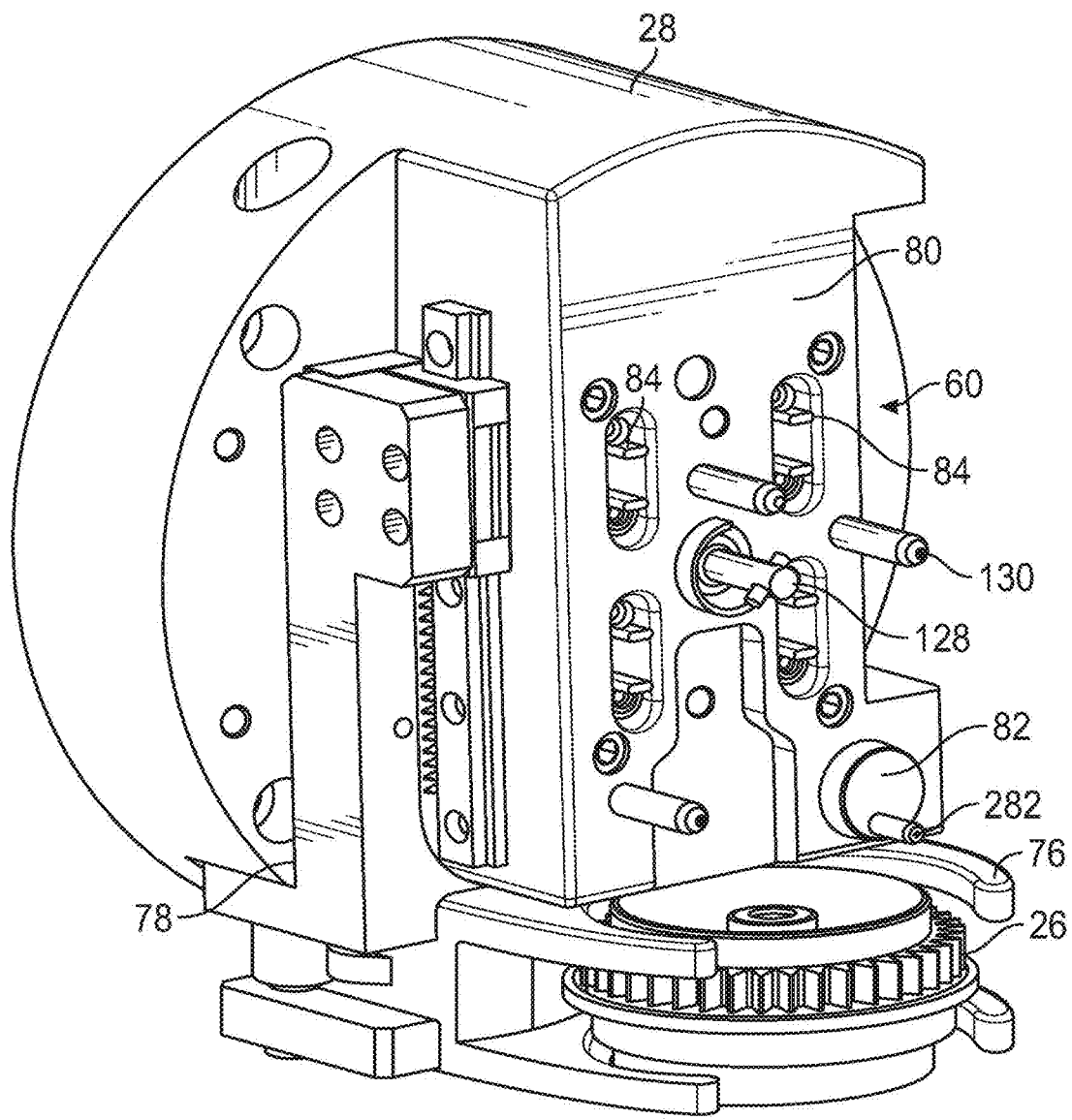
FIG. 14 illustrates a perspective view of the pump head assembly, gripping system and vial puck of FIG. 13 in accordance with aspects of the present disclosure.
Figure 15:
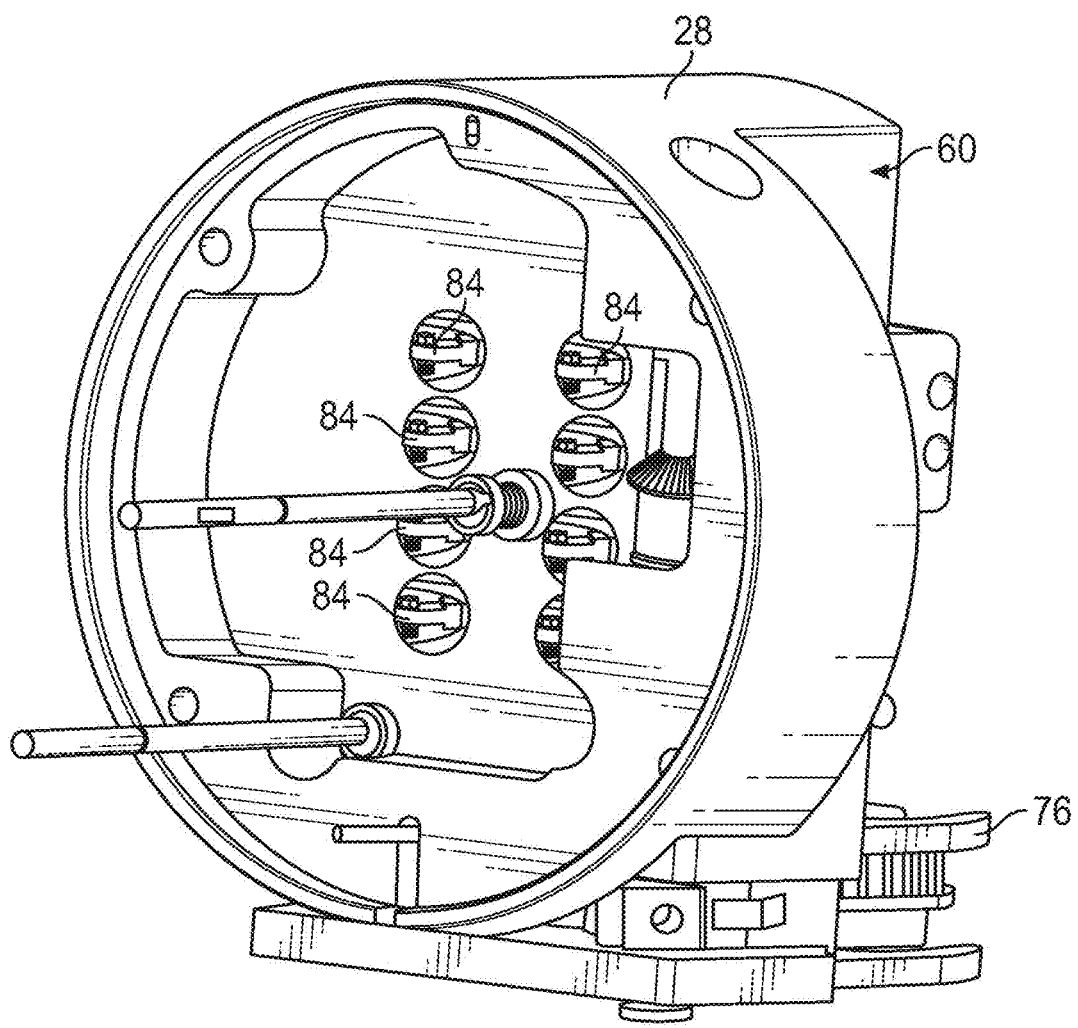
FIG. 15 illustrates a rear perspective view of the pump head assembly, gripping system and vial puck of FIG. 13 in accordance with aspects of the present disclosure.
Figure 16:
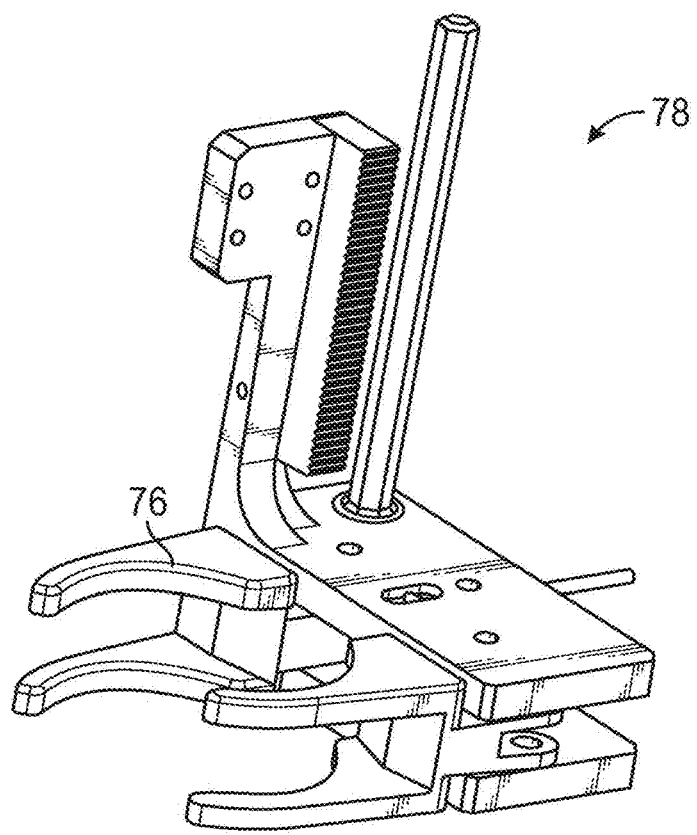
FIG. 16 illustrates a perspective view of an exemplary embodiment of a gripping system in accordance with aspects of the present disclosure.
Figure 17:
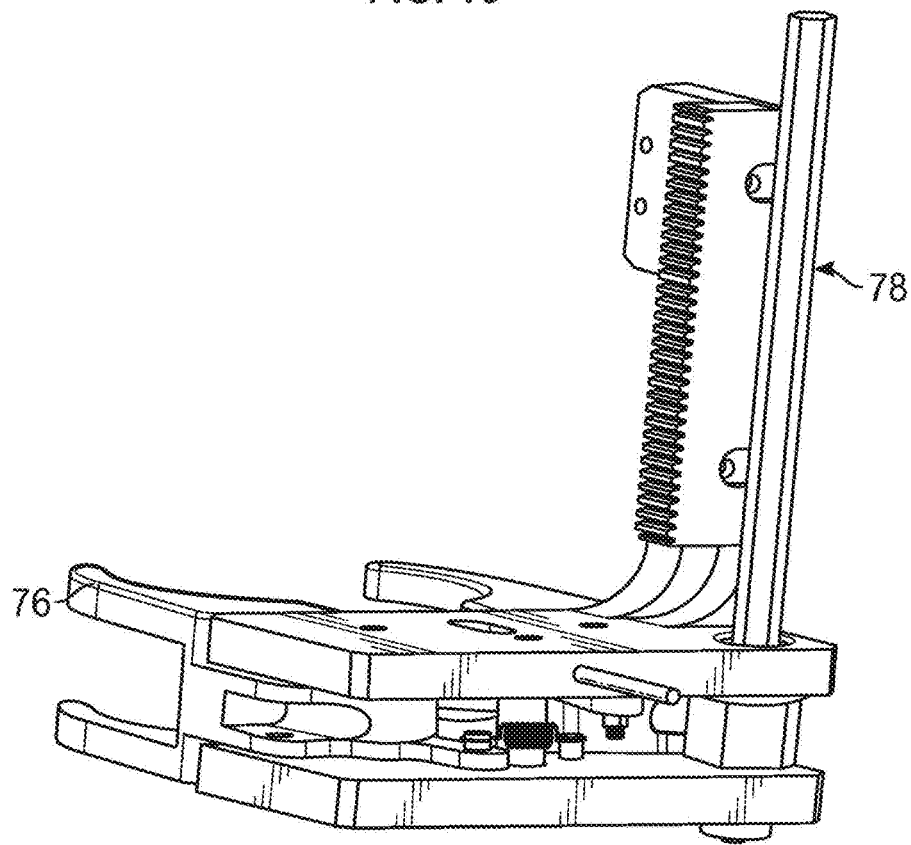
FIG. 17 illustrates a rear perspective view of the gripping system of FIG. 16 in accordance with aspects of the present disclosure.
Figure 18:
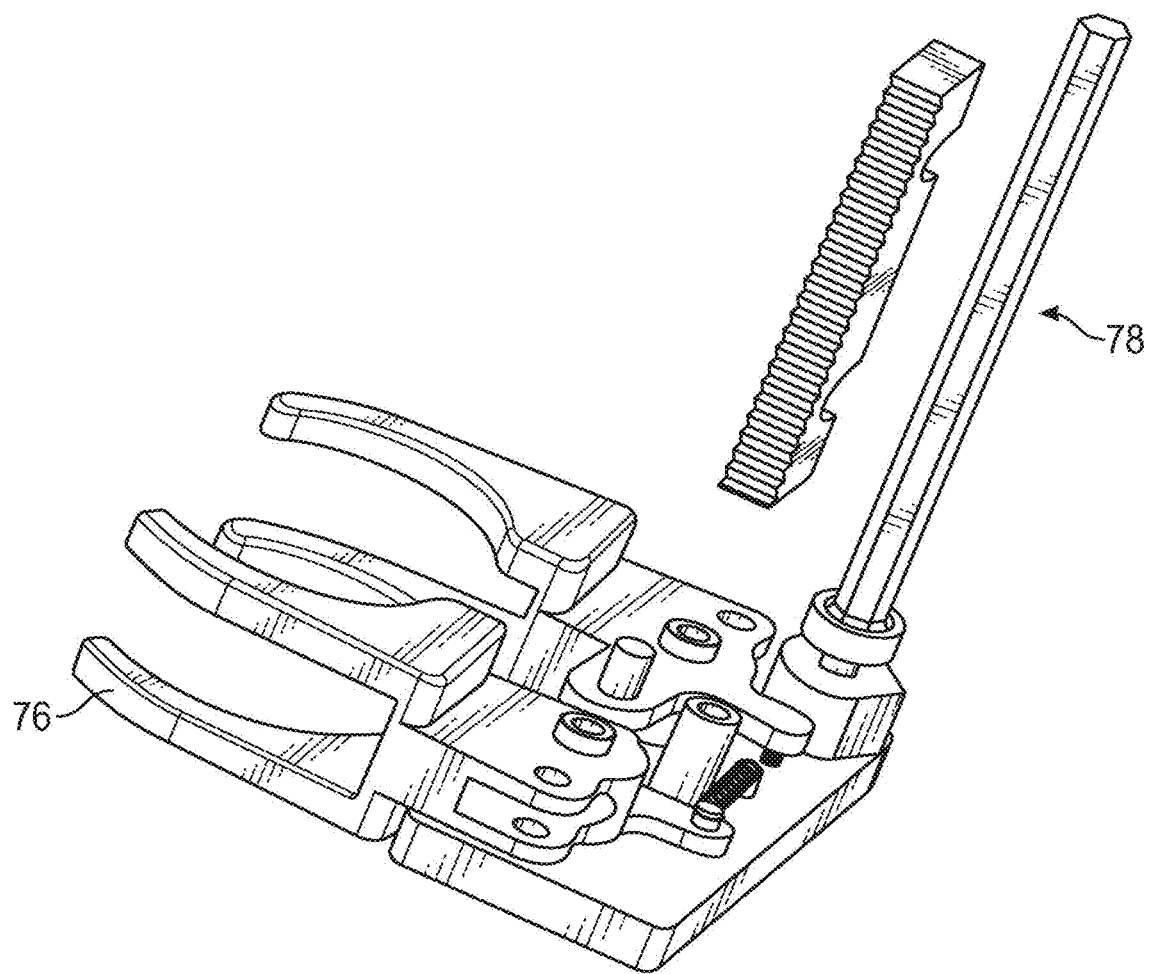
FIG. 18 illustrates a side perspective view of the gripping system of FIG. 16 in accordance with aspects of the present disclosure.
Figure 19:
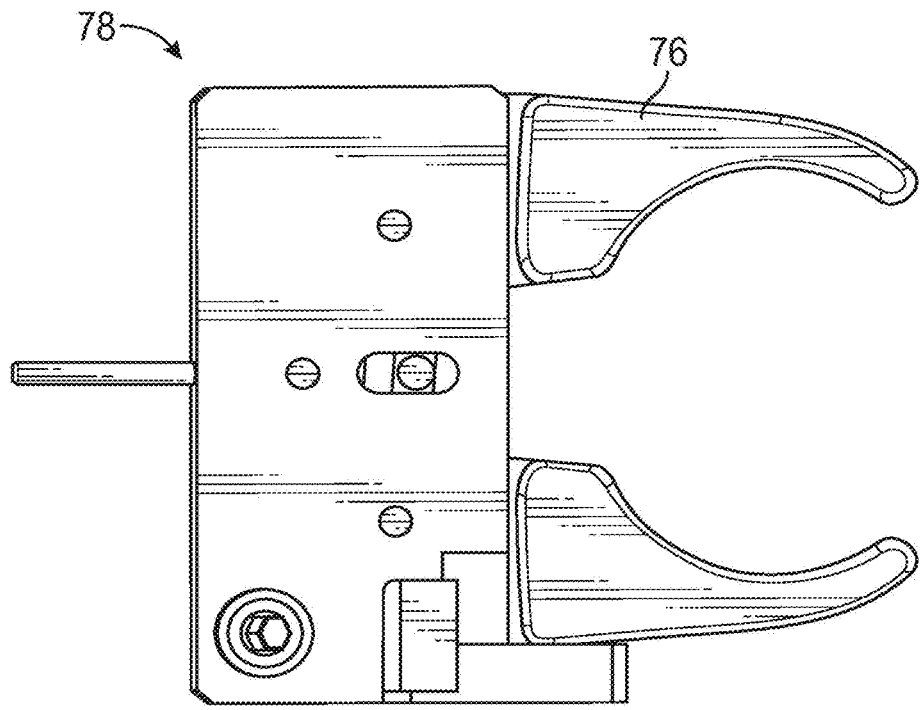
FIG. 19 illustrates a top plan view of the gripping system of FIG. 16 in accordance with aspects of the present disclosure.
Figure 20:
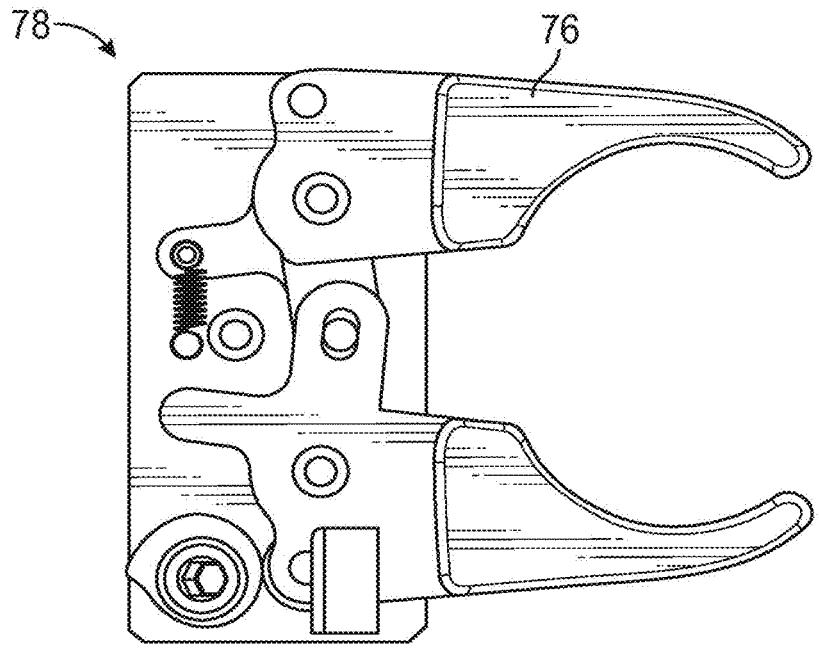
FIG. 20 illustrates a top plan view of the gripping system of FIG. 16 in accordance with aspects of the present disclosure.

Next to the rotation housing 46 is the motor mount 54, which is shown alone from various angles in FIGS. 6-8, according to an embodiment. In the embodiment shown in FIGS. 4-8, the cam housing 56, shown in further details from various angles FIGS. 9-11, is connected to the motor mount 54, which includes cams and gears that control the rotary motion of the motors and the axial motion of the pump drive mechanism 20 as it moves into position to pick up a cartridge 16 and a vial 18.

The compounder system also includes a diluent magazine (not shown) that mounts in a slot 60 located on the side of the pump drive mechanism. The diluent magazine may be a disposable piece configured to receive any number of individual diluent manifolds operable as diluent ports. The diluent manifolds (not shown) may be modular so they can easily and removably connect to each other, the magazine, and/or connect to the pump drive mechanism 20.

The final portion of the pump drive mechanism 20 is the pump head assembly 28. The pump head assembly 28 includes the vial grasping arms 76, the vial lift 78, the pump cartridge grasp 80, the pump piston eccentric drive shaft 82 with arm 222, the valve actuation mechanisms 84, as well as the motors that allow the pump drive mechanism 20 to move forward and back and to rotate in order to mix the pharmaceutical in the vial 18 once the diluent has been added to it. The compounder 10 may also include an input screen 86 such as a touch screen 86 as shown in the figures to provide data entry by the user and notifications, instructions, and feedback to the user.

Figure 21:
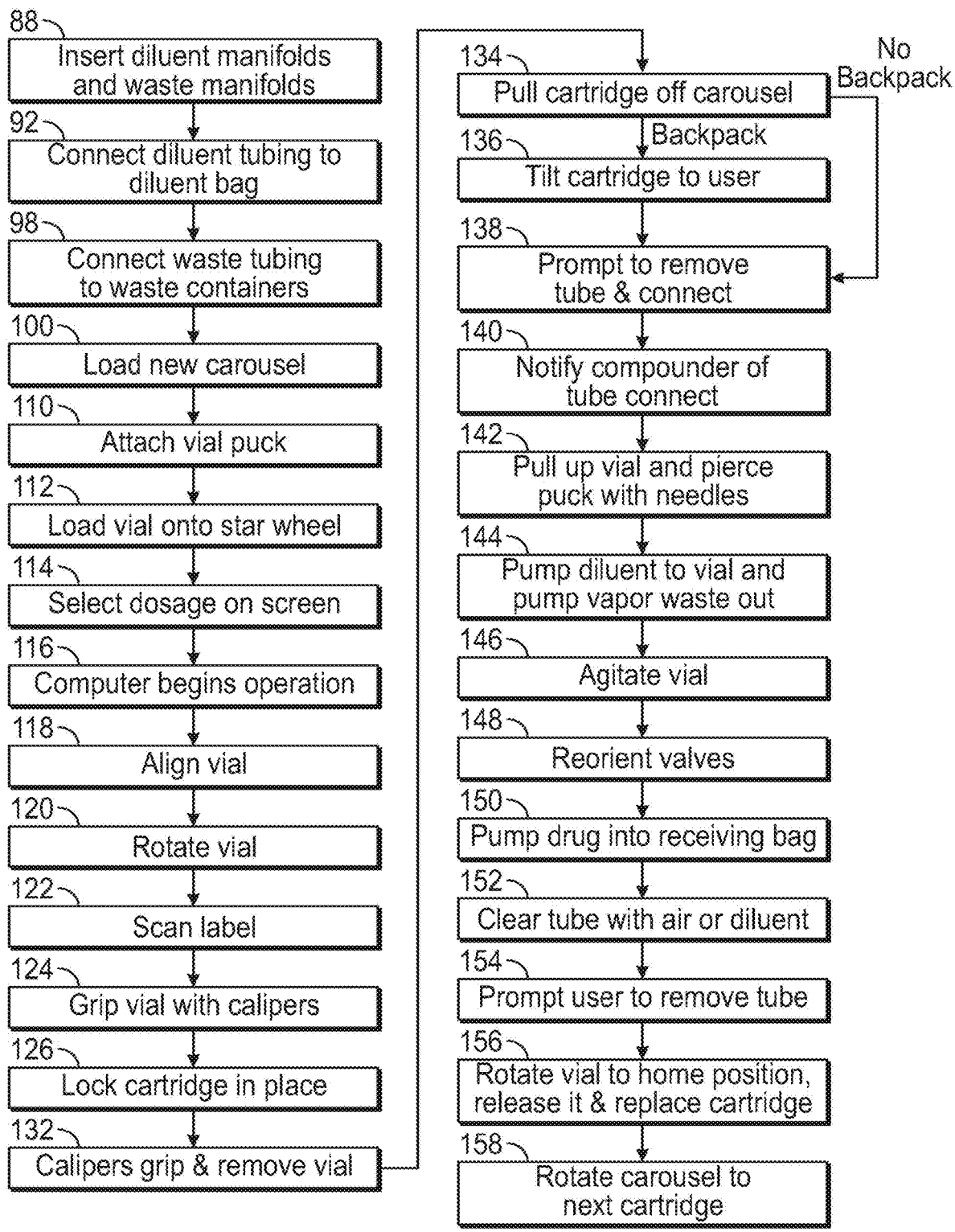
FIG. 21 is a flow chart illustrating an exemplary embodiment of the steps of a process in accordance with aspects of the present disclosure.

The operation of the compounder system 10 will now be generally described in the flowchart illustrated at FIG. 21, according to an embodiment. In the first step 88, a user inserts a new diluent manifold magazine having a plurality of manifolds (e.g., diluent manifolds and waste manifolds) into the slot 60 on the side of the pump head assembly 28. Manifolds may be loaded into the magazine before or after installing the magazine in the slot 60. The manifolds maintain needles inside the housing of the manifold until the cartridge 16 is later locked in place. The magazine may contain any number of diluent manifolds and vapor waste manifolds. In one illustrative system, there may be three diluent manifolds and one vapor waste manifold. In the next step 92, diluent tubing is connected to corresponding diluent bags. The tubes may be routed through locking flanges on a surface (e.g., the front surface) of the compounder frame to hold them in place. For example, in the illustrated embodiment of FIG. 24, the tubes are held in place with locking flanges 2402 on the frame of the compounder. Alternatively, other types of clips or locking mechanisms known in the art may be used to hold the tubes securely in place. In the illustrated embodiment of FIG. 4, the additional flanges 94 positioned on the outside housing 96 of the pump drive mechanism 20 are provided for securing internal wiring of the compounder. In the next step 98, waste tubing may be connected to the vapor waste bag 44. In other embodiments, tubing may be pre-coupled between the manifolds and associated containers such as diluent containers and/or waste containers and the operations of steps 92 and 98 may be omitted.

If desired, in the next step 100, a new carousel 14 may be loaded into a carousel mounting station such as a carousel hub of the compounder system. The carousel 14 may contain any number of disposable cartridges 16 arranged in a generally circular array. In the next step 110, a vial puck 26 is attached to the top of a vial 18 of a powdered or liquid pharmaceutical for reconstitution and the vial 18 is loaded into the star wheel 22 under the carousel 14 in the next step 112. Step 110 may include loading multiple vials 18 into multiple vial puck recesses in star wheel 22. After one or more vials are loaded into the star wheel, the vials are rotated into position to enable and initiate scanning of the vial label of each vial. In one embodiment, the user will be allowed to load vials into the star wheel until all vial slots are occupied with vials before the scanning is initiated. A sensor may be provided that detects the loading of each vial after which a next vial puck recess is rotated into the loading position for the user. Allowing the user to load all vials into the star wheel prior to scanning of the vial labels helps increase the efficiency of compounding. However, in other implementations, scanning of vial labels may be performed after each vial is loaded or after a subset of vials is loaded. Following these setup steps, the next step 114 is for a user to select the appropriate dosage on the input screen.

After the selection on the input screen 86, the compounder 10 begins operation 116. The star wheel 22 rotates the vial into alignment 118 with the vial grasping calipers 76 of the pump head assembly 28. The vial puck 26 includes, for example, gears that interface with gears coupled to a rotational motor that allow the vial 18 to rotate 120 so that a scanner (e.g., a bar code scanner or one or more cameras) can scan 122 a label on the vial 18. The scanner or camera (and associated processing circuitry) may determine a lot number and an expiration date for the vial. The lot number and expiration date may be compared with other information such as the current date and/or recall or other instructions associated with the lot number. Once the vial 18 is scanned and aligned, in the next step 124 the pump drive mechanism 20 moves forward into position to grip the vial 18 with the calipers 76. The forward movement also brings the mounting posts 130 and locking bayonet 128 on the front of the pump head assembly 28 into matching alignment with corresponding openings on a cartridge 16. In the next step 126 the cartridge 16 is locked in place on the pump head assembly 28 with the locking bayonet 128 and the calipers 76 grip 132 the vial puck 26 on the top of the vial 18. The calipers 76 then remove 132 the vial 18 from the star wheel 22 by moving backward, while at the same time pulling 134 the cartridge 16 off of the carousel 14.

In some embodiments, the cartridge 16 includes a backpack that includes a coiled tube. In this embodiment, in step 136 the pump drive mechanism 20 tilts the cartridge 16 toward the user to expose the end of the tube and prompts 138 the user to pull the tube out of the backpack and connect it to the receiving bag 32. In an alternative embodiment, the tube 38 is exposed on the side of the carousel 14 once the cartridge 16 is pulled away from the carousel 14. In another alternative embodiment, the tube 38 is automatically pushed out (e.g., out of the backpack) thus allowing the user to grab onto the connector located at the end of the tube and connect to the receiving container. The system prompts 138 the user to pull the tube out from the carousel 14 and connect it to the input 34 of the IV bag 32. Once the tube 38 is connected, in step 140 the user may notify the compounder 10 to continue the compounding process by interacting with the input screen 86.

At step 142, the vial 18 is pulled up towards the cartridge 16 so that one or more needles such as a coaxial dual lumen needle of the cartridge 16 pierce the top of the vial puck 26 and enter the interior of the vial 18. Although the example of FIG. 21 shows engagement of the needle with the vial puck after the user attaches the tube from the cartridge to the receiving container, this is merely illustrative. In another embodiment, steps 138 and 140 may be performed after step 142 such that engagement of the needle with the vial puck occurs before the user attaches the tube from the cartridge to the receiving container.

Diluent is pumped at step 144 into the vial 18 through the cartridge 16 and a first needle in the proper dosage. If necessary, a second or third diluent may be added to the vial 18 via a second or third diluent manifold attached to the cartridge 16. Simultaneously, vapor waste is pumped 144 out of the vial 18, through a second needle, through the cartridge 16 and the vapor waste manifold, and into the vapor waste bag 44. The valve actuators 84 on the pump head assembly 28 open and close the valves of the cartridge 16 in order to change the fluid flow paths as necessary during the process. Once the diluent is pumped into the vial 18, the pump drive mechanism 20 agitates the vial 18 in the next step 146 by rotating the vial lift 78 up to, for example 180 degrees such that the vial 18 is rotated between right-side-up and upside-down positions. The agitation process may be repeated for as long as necessary, depending on the type of pharmaceutical that is being reconstituted. Moreover, different agitation patterns may be used depending on the type of drugs being reconstituted. For example, for some drugs, rather than rotating by 180 degrees, a combination of forward-backward, and left-right motion of the pump head may be performed to generate a swirling agitation of the vial. A plurality of default agitation patterns for specific drugs or other medical fluids may be included in the drug library stored in (and/or accessible by) the compounder control circuitry. Once the agitation step is complete, the pump drive mechanism rotates the vial to an upside down position or other suitable position and holds it in place. In some embodiments, a fluid such as a diluent already in the receiving container 32 may be pumped (e.g., through the cartridge or via a separate path) into a liquid waste container to allow room in the receiving container for receiving the reconstituted medicine.

In the next step 148, the valve actuators 84 reorient the valves of the cartridge and the pumping mechanism of the cartridge 16 is activated to pump 150 the reconstituted drug into the receiving bag 32 through the attached tube. Once the drug is pumped into the receiving bag 32, in the next step 152 the pump drive mechanism 20 clears the tube 38 by either pumping filtered air or more diluent through the tube 38 into the receiving bag 32 after another valve adjustment to ensure that all of the reconstituted drug is provided to the receiving bag 32. In some scenarios, a syringe may be used as a receiving container 32. In scenarios in which a syringe is used as the receiving container 32, following delivery of the reconstituted drug to the syringe, a vacuum may be generated in tube 38 by pump drive mechanism 20 to remove any air or other vapors that may have been pushed into the syringe so that, when the syringe is removed from tube 38, the reconstituted drug is read for delivery to a patient and no air or other unwanted gasses are present in the syringe.

The system then prompts 154 the user to remove the tube 38 from the receiving container 32. The user may then insert the connector (e.g., a Texium® or SmartSite® connector) into its slot in the backpack or carousel and an optical sensor in the pump head may sense the presence of the connector and automatically retract the tube into either the carousel or the backpack. The tube is pulled back into either the carousel 14 or the backpack, depending on which type of system is in use. In the next step 156, the compounder 10 rotates the vial 18 back into alignment with the star wheel 22 and releases it. The used cartridge 16 may also be replaced on the carousel 14. The used cartridge may be released when a sensor in the pump drive determines that the tube has been replaced in the cartridge (e.g., by sensing the presence of a connector such as a Texium® connector at the end of the tube in the backpack of the cartridge through a window of the cartridge). The carousel 14 and/or star wheel 22 then may rotate 158 to a new unused cartridge 16 and/or a new unused vial 18 and the process may be replicated for a new drug. In some circumstances (e.g., multiple reconstitutions of the same drug), a single cartridge may be used more than once with more than one vial.

The cartridges 16 are designed to be disposable, allowing a user to utilize all the cartridges 16 in a given carousel 14 before replacing the carousel 14. After a cartridge 16 is used, the carousel 14 rotates to the next cartridge 16, and the system software updates to note that the cartridge 16 has been used, thus preventing cross-contamination from other reconstituted drugs. Each cartridge 16 is designed to contain all the necessary flow paths, valves, filters and pumps to reconstitute a drug with multiple diluents if necessary, pump the reconstituted drug into the receiving container, pump vapor waste out of the system into a waste container, and perform a final QS step in order to make sure that the proper amount of drug and diluent is present in the receiving container. This complete package is made possible by the specific and unique construction of the cartridge 16, its flow paths, and its valve construction.

Figure 22:
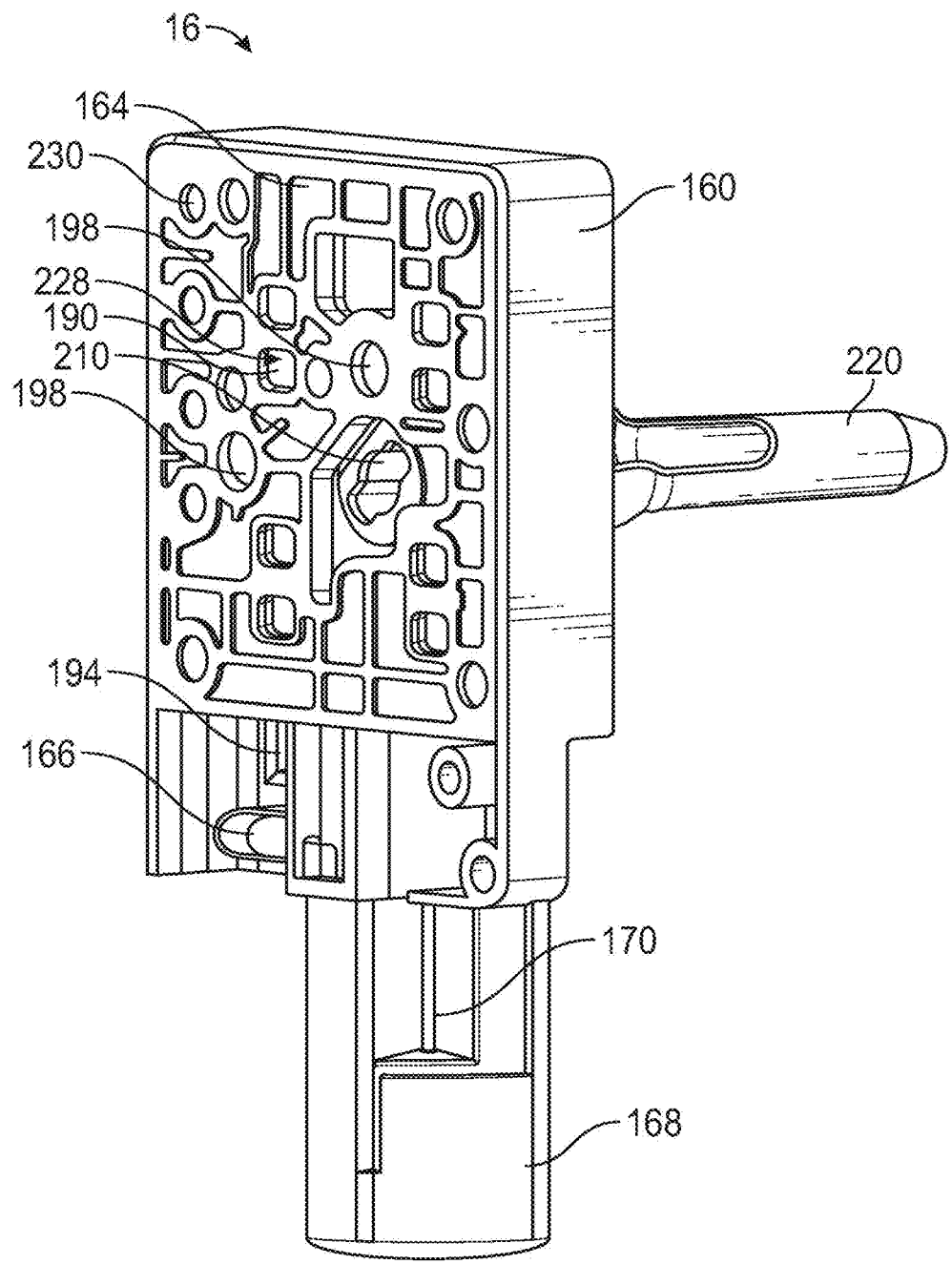
FIG. 22 illustrates a perspective view of an exemplary embodiment of a cartridge in accordance with aspects of the present disclosure.

An embodiment of a cartridge 16 is illustrated in FIG. 22. As shown in FIG. 22, cartridge 16 may include a cartridge frame 160, a cartridge bezel 164, as well as a piston pump 166, a needle housing 168 and a needle assembly 170. The cartridge frame 160 provides the main support for each cartridge 16 and includes diluent chambers, a vapor waste chamber, a pumping chamber, a hydrophobic vent, an exit port, and/or other features as described hereinafter that can be connected to a tube that connects to the receiving container 32.

The frame 160 of the cartridge 16 also includes locating features that allow each cartridge 16 to be removably mounted to the pump head assembly 28. These features include, for example, three openings 198 to receive mounting posts 130 from the pump head assembly 28, and a keyhole 210 that allows a locking bayonet 128 to be inserted therein and turned to lock the cartridge 16 to the pump head assembly 28 for removal from the carousel 14. An outlet port extension 220 may be present in some embodiments. The piston pump 166 is mounted within a chamber with a rod 194 positioned within a silicone piston boot. Furthermore, the bezel 164 includes openings 228 in which the valves 190 of the sealing membrane are located and be accessed by the valve actuators 84. Bezel 164 may also include an opening that facilitates the detection of a connector (e.g., a Texium® or SmartSite® connector) when the user inserts the connector into the provided slot when compounding is complete. Moreover, the bezel 164 includes openings 230 that allow a fluid manifold to be connected to the diluent and vapor waste chambers in the cartridge 16. In operation, the needles of the fluid manifold enter through the openings 230 in the bezel 164 and pierce the sealing membrane to gain fluidic access to the diluent and vapor waste chambers defined in the cartridge 16 between the sealing membrane and the cartridge frame 160. Further details of various embodiments of the cartridge 16 will be discussed hereinafter.

Figure 23:
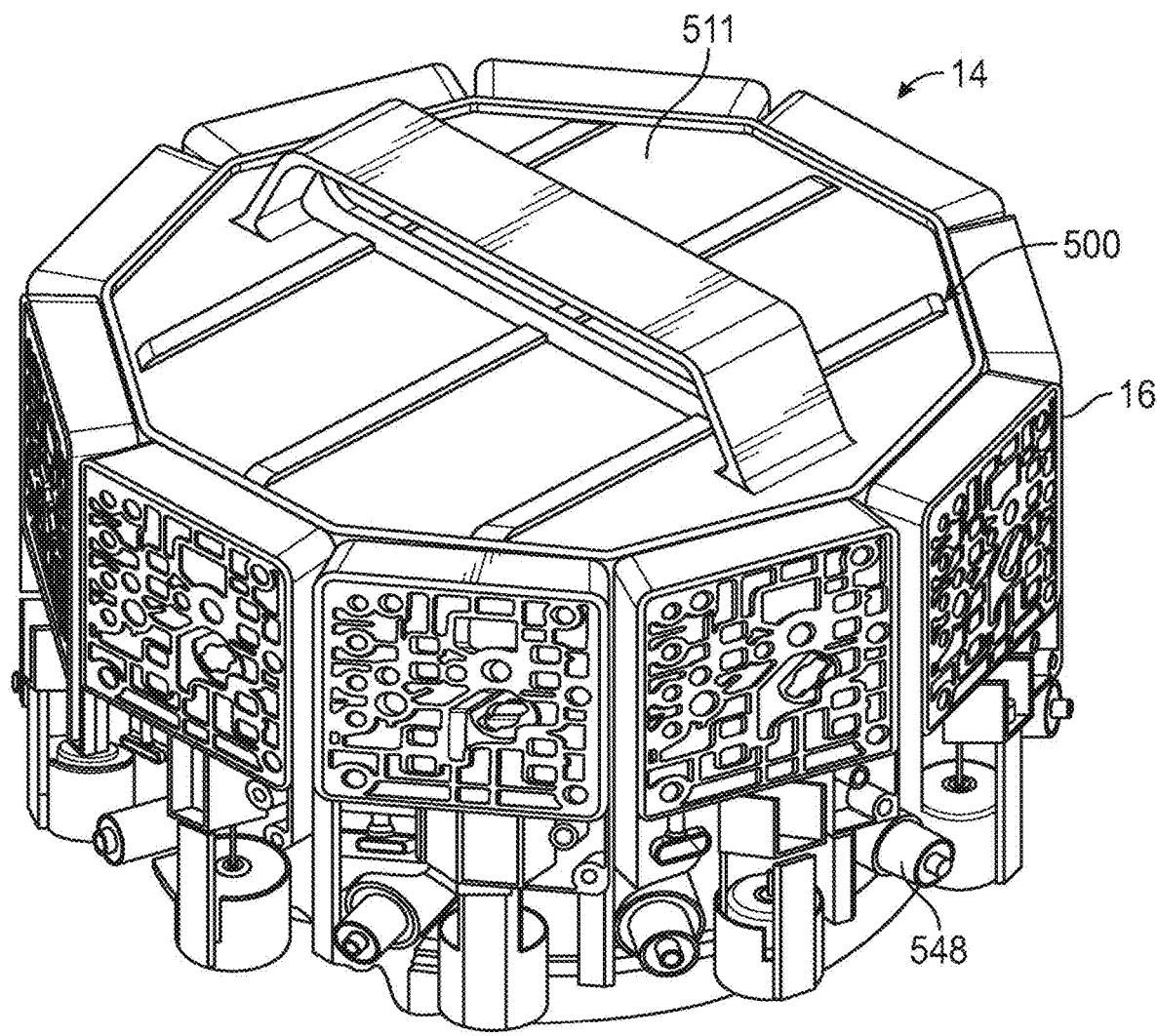
FIG. 23 illustrates a perspective view of an exemplary embodiment of a carousel with a cover in accordance with aspects of the present disclosure.

Referring to FIG. 23, an exemplary embodiment of a carousel 14 removed from the compounder 10 is illustrated, according to an embodiment. The carousel 14 of FIG. 23 includes an array of ten cartridges 16 in this embodiment, but it should be understood that more or fewer cartridges 16 can be present on the carousel 14, leaving some of the carousel 14 pockets 500 empty, or the frame 510 of the carousel can be designed to have more or fewer cartridge pockets 500. The carousel 14 also includes a cover 511 that prevents a user from accessing the tubes coupled to each of the cartridges 16 directly. The cover 511 may be removed if necessary to access the backs of the cartridges 16. In the example implementation of FIG. 23, a connector such as a Texium® attachment 548 is disposed adjacent each cartridge 16, the attachment 548 being attached to the tube 38 that runs from the extension 220 on each cartridge 16.

Figure 24:
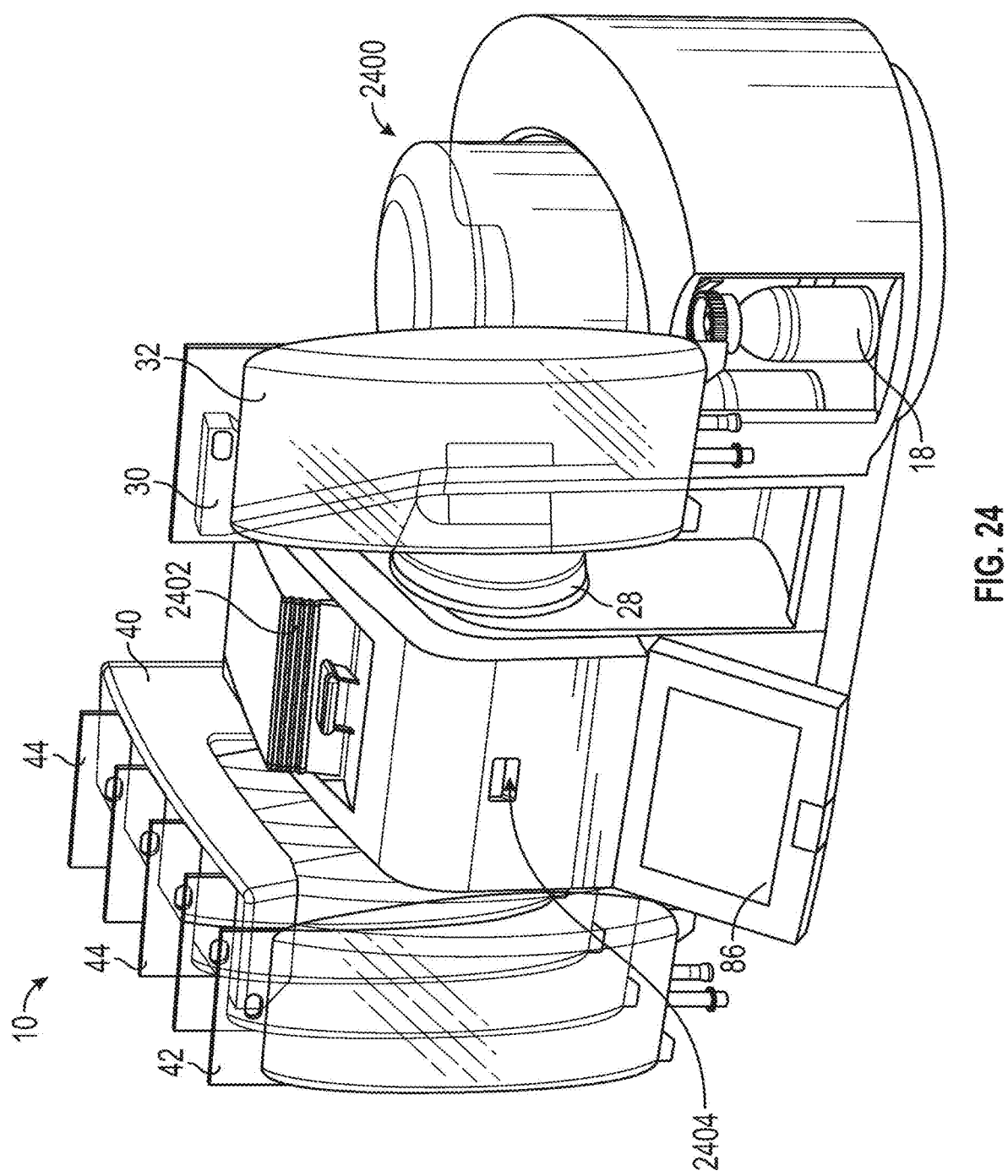
FIG. 24 illustrates a front perspective view of another exemplary embodiment of a compounding system in accordance with aspects of the present disclosure.

FIGS. 24-29 show the compounder 10 according to another embodiment. As shown in FIG. 24, holding apparatus 40 may be implemented as an extended arm providing support for mounting devices for each of containers 42 and 44. Holding apparatus 40 and holding apparatus 30 may each include one or more sensors such as weight sensors configured to provide weight measurements for determining whether an appropriate amount of fluid has been added to or removed from a container or to confirm that fluid is being transferred to and/or from the appropriate container (e.g., that the appropriate diluent is being dispensed). A scanner 2404 may be provided with which each diluent container and/or the receiving container can be scanned before and/or after attachment to compounder 10. As shown in FIG. 24, a carousel cover 2400 and tube management structures 2402 may also be provided on compounder 10 in various embodiments. For example, tubes connected between containers 42 and/or 44 and corresponding manifolds can each be mounted in a groove of tube management structure 2402 to prevent tangling or catching of the tubes during operation of compounder 10.

Figure 25:
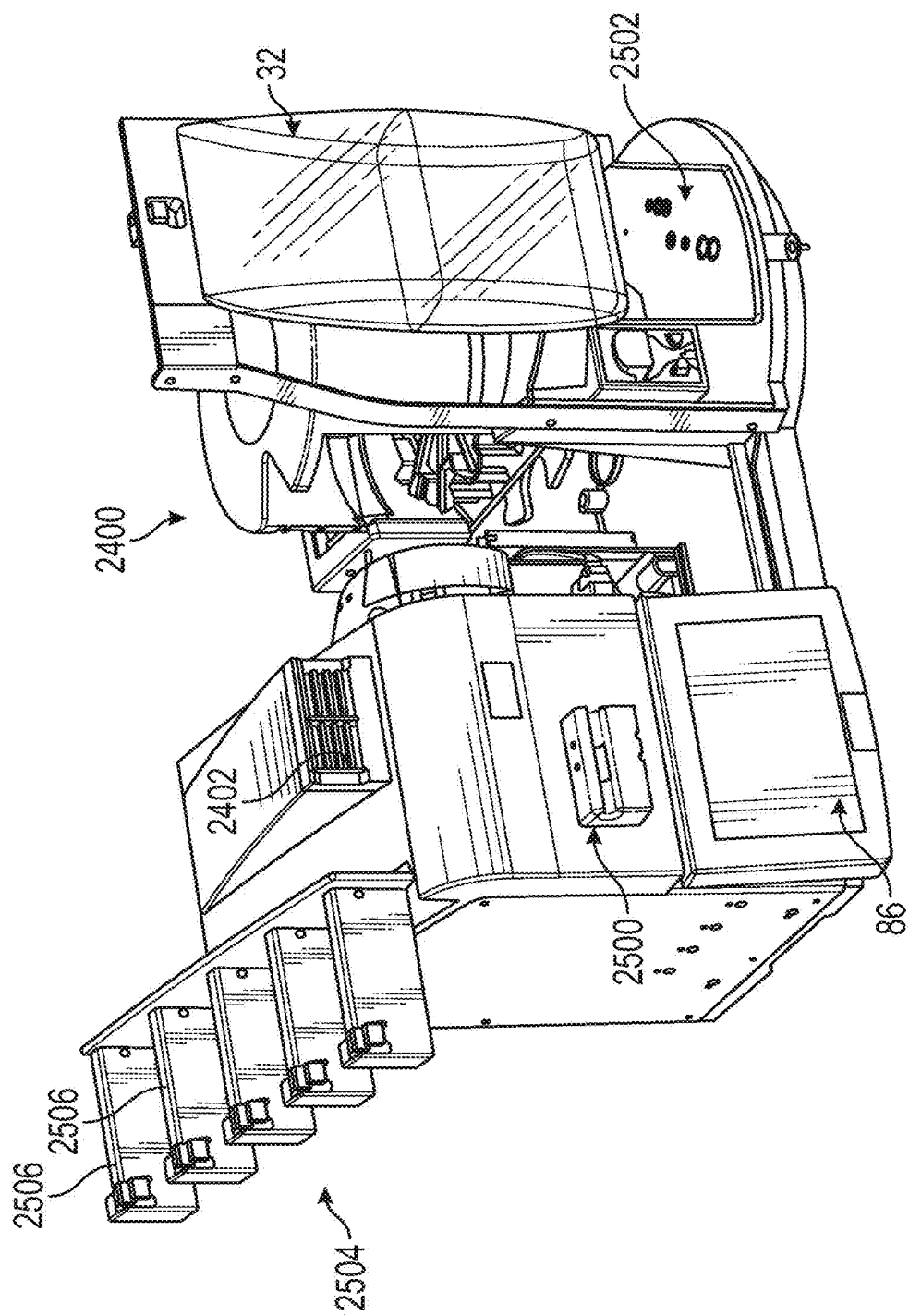
FIG. 25 illustrates another front perspective view of the compounding system of FIG. 24 in accordance with aspects of the present disclosure.

As shown in FIG. 25, an opening 2502 may be provided by which vials 18 can be installed in the star wheel. Additionally, an exterior pump 2500 may be provided for pumping non-toxic liquid waste from, for example, receiving container 32 to a waste container 44 (e.g., for pumping a desired amount of saline out of receiving container 32 quickly and without passing the liquid waste through a cartridge and/or other portions of the compounder).

A fluidics module 2504 may be provided that includes several container mounts 2506. Container mounts 2506 may be used for hanging diluent and waste containers and may include sensor circuitry for sensing when a container has been hung and/or sensing the weight of the container. In this way, the operation of compounder 10 can be monitored to ensure that the correct diluent contain has been scanned and hung in the correct location and that the waste is being provided in an expected amount to the appropriate waste container.

Figure 26:
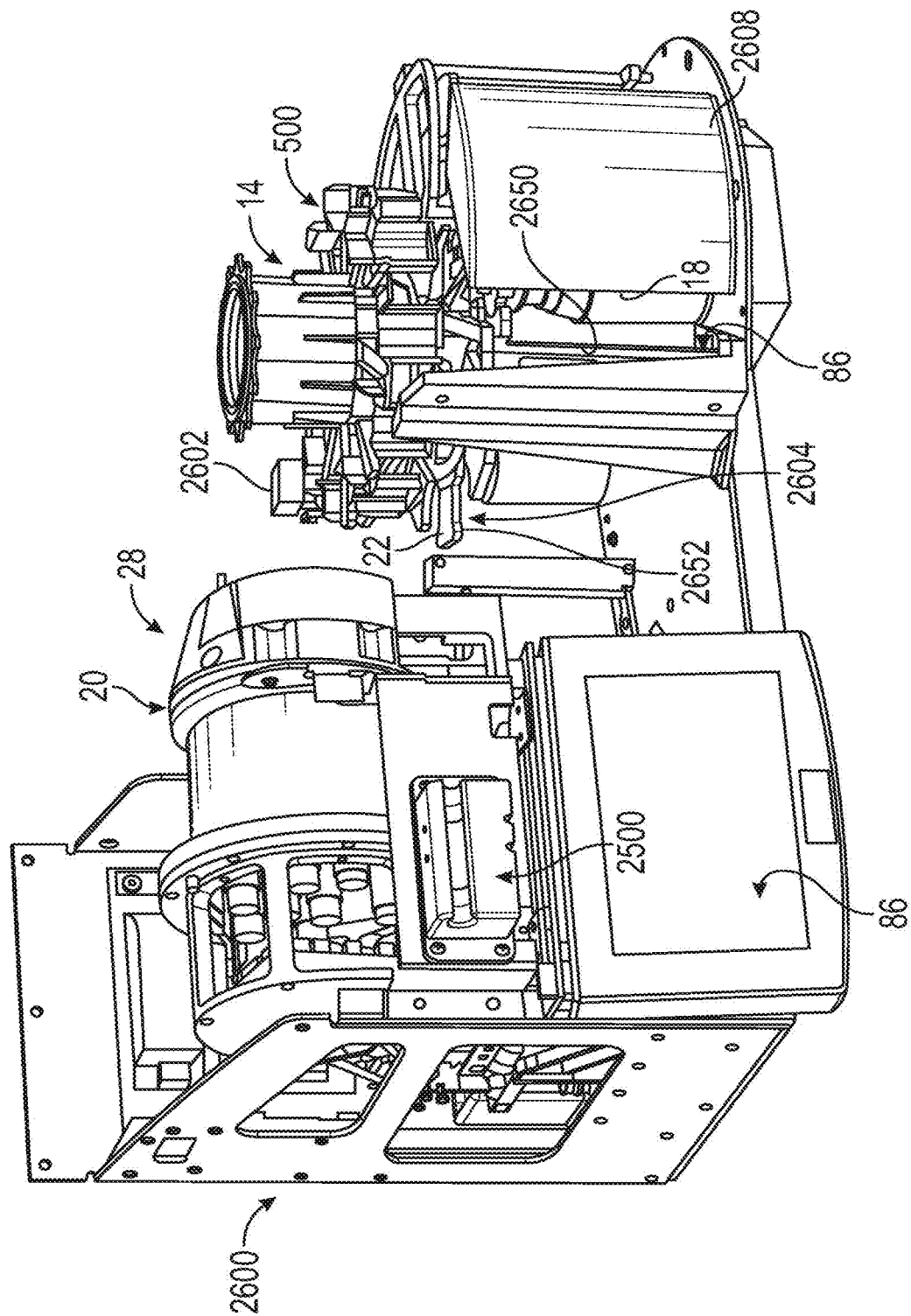
FIG. 26 illustrates a front perspective view of the compounding system of FIG. 24 with portions of the housing removed in accordance with aspects of the present disclosure.

As shown in FIG. 26, pump 2500 and display 86 may be mounted to a chassis 2600. Pump drive 20 may be mounted partially within the chassis 2600 with pump head assembly 28 extending from the chassis to a position which allows the pump head assembly to rotate (e.g., to turn over or agitate a vial). Carousel 14 is also shown in FIG. 26 without any cartridges mounted therein so that cartridge mounting recesses 500 can be seen.

Star wheel 22 (sometimes referred to herein as a vial tray) is shown in FIG. 26 with several empty vial puck recesses 2604. Vial tray 22 may be rotated and an actuating door 2608 may be opened to facilitate loading of vials 18 into the vial puck recesses 2604 in vial tray 22. In some embodiments, door 2608 may be closed before rotation of vial tray 22 to ensure that the operator's fingers are not in danger of injury from the rotating tray. However, this is merely illustrative. In other embodiments a sensor such as sensor 2650 (e.g., a light curtain) may be provided instead of (or in addition to) door 2608 to sense the presence of an operator in the vicinity of tray 22 and prevent rotation of the tray if the operator or any other obstruction is detected.

Similarly, a lid may be provided for carousel 14 to prevent contamination of cartridges 16 loaded therein, and to prevent injury to an operator due to rotation of the carousel. A lid sensor (not shown) may also be provided to detect the position (e.g., an open position or a closed position) of the lid. Rotation of carousel 14 may be prevented if the lid is not detected in a closed position by the lid sensor.

Each vial 18 that is inserted may be detected using a sensor such as sensor 2652 (e.g., a load sensor or an optical sensor) when placed in a vial puck recess 2604. When detected, the inserted vial may be moved to a scanning position by rotating vial tray 22 and then the inserted vial 18 may be rotated within its position in vial tray 22 using a vial rotation motor 2602 to allow the vial label to be scanned.

Figure 27:
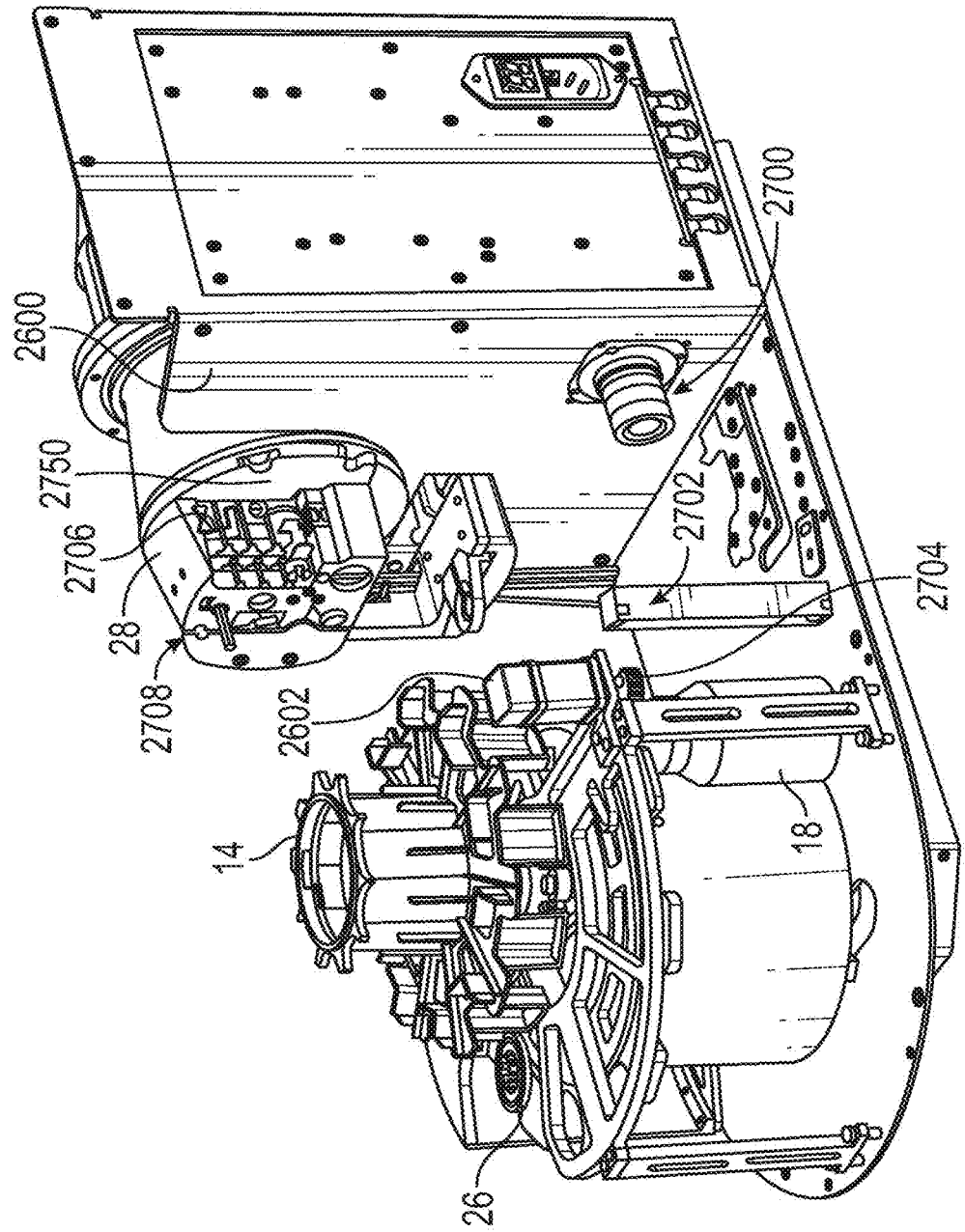
FIG. 27 illustrates a rear perspective view of the compounding system of FIG. 24 with portions of the housing removed in accordance with aspects of the present disclosure.

A reverse perspective view of compounder 10 is shown in FIG. 27 in which scanning components can be seen. In particular, a camera 2700 is mounted in an opening in chassis 2600 and configured to view a vial 18 in a scanning position. Motor 2602 may rotate vial 18 through one or more full rotations so that camera 2700 can capture images of the vial label. In some embodiments, an illumination device 2702 (e.g., a light-emitting diode or other light source) may be provided that illuminates vial 18 for imaging with camera 2700.

As shown in FIG. 27 one or more gears 2704 coupled to motor 2602 may be provided that engage corresponding gears on a vial puck 26 to which a vial 18 is attached at the scanning position. The vial tray 22 may be rotated so that the vial puck gears engage the rotation motor gears so that when the motor 2602 is operated the vial 18 is rotated.

FIG. 27 also shows how a magazine 2706 containing one or more manifolds may be mounted in a recess in pump head assembly 28. A magazine slot in magazine 2706 for the vapor waste manifold may be keyed to prevent accidental connection of a diluent manifold in that slot (or a waste manifold in a diluent slot in the magazine). Other diluent slots in magazine 2706 may have a common geometry and thus any diluent manifold can fit in the magazine diluent slots. One or more manifold sensors such as manifold sensor 2750 (e.g., an optical sensor) may be provided in the manifold recess in pump head assembly 28. Manifold sensor 2750 may be configured to detect the presence (or absence) of a manifold in a manifold recess (slot) in magazine 2706 to ensure that an appropriate manifold (e.g., a diluent manifold or waste manifold) is loaded at the expected position for compounding operations. In this way, the pump head may detect a manifold presence. The pump head and/or manifold sensors may communicate with the diluent load sensors to ensure proper positioning of the diluent manifolds. Various operational components 2708 such as valve actuators, needle actuators, mounting posts, a locking bayonet, and a drive pin (e.g., as described above in connection with FIG. 4) can also be seen extended from pump head assembly 28 which are configured to secure and operate a pump cartridge 16.

Figure 28:
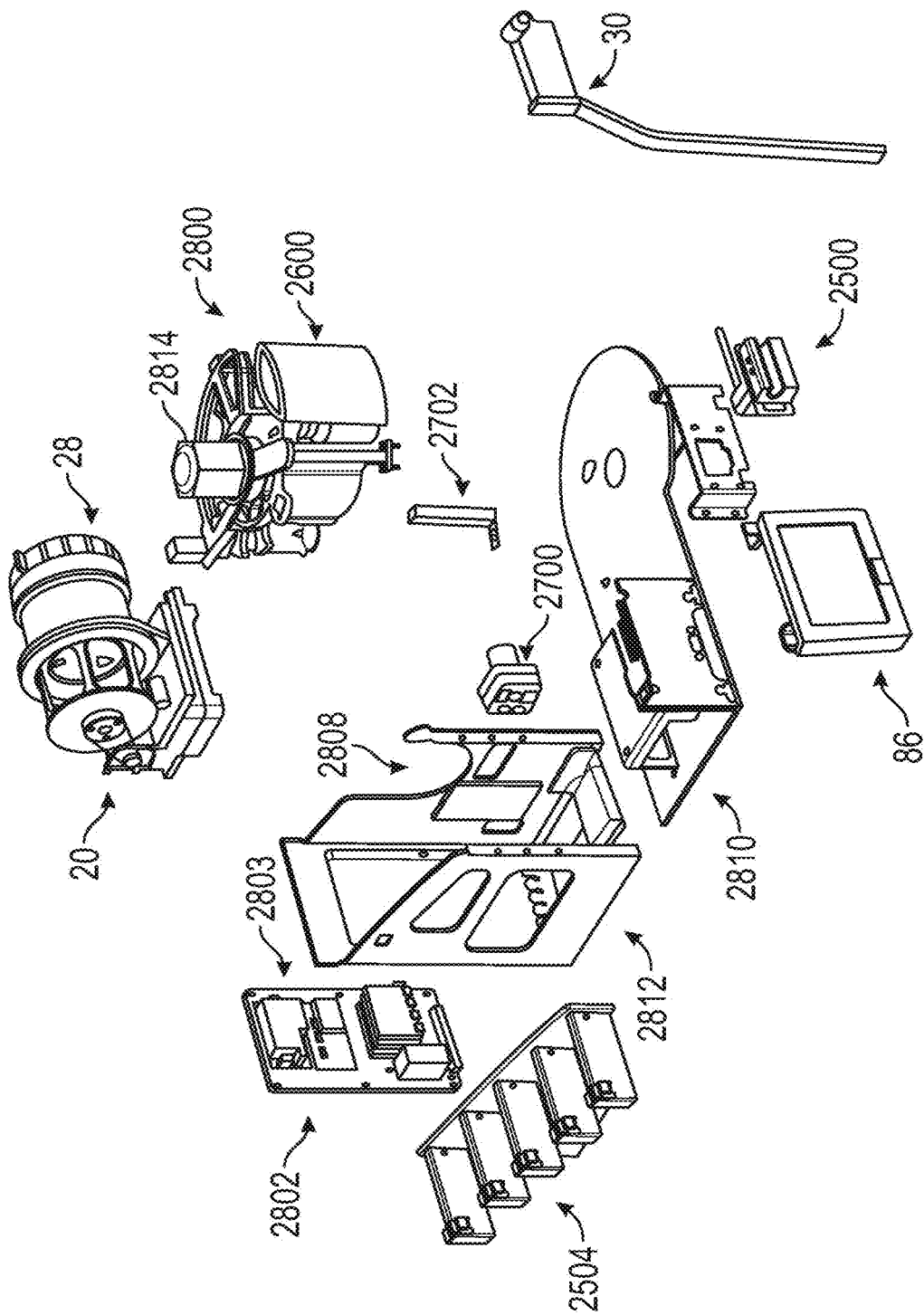
FIG. 28 illustrates an exploded perspective view of the compounding system of FIG. 24 in accordance with aspects of the present disclosure.

An exploded view of various components of compounder 10 is shown in FIG. 28. Components discussed above such as display 86, pump 2500, dose hanger 30, fluidics module 2504, pump drive 20 with pump head assembly 28, camera 2700, and lighting device 2702 are shown. Additional components such as a chassis base 2810 and chassis housing 2812 of chassis 2600 are also shown in FIG. 28. A rear panel 2802 having an electronics assembly 2803 can be mounted to chassis housing 12 and pump drive 20 may be seated in an opening 2808 in chassis housing 2812 that allows pump head assembly 28 to protrude from chassis housing 2812. Processing circuitry for managing operations of compounder system 10 may be included in electronics assembly 2803.

A vial tray and carousel drive assembly 2800 is also shown in which actuating door 2608 and a carousel hub 2814 can be seen. Carousel 14 may be placed onto carousel hub and rotated by vial tray and carousel drive assembly 2800 operating to rotate hub 2814 to move a selected cartridge in the carousel into position to be retrieved and operated by pump drive 20. Vial tray and carousel drive assembly 2800 may include separate drive assemblies for the vial tray and for the carousel such that vial tray 22 and carousel 14 may be rotated independently.

Figure 29:
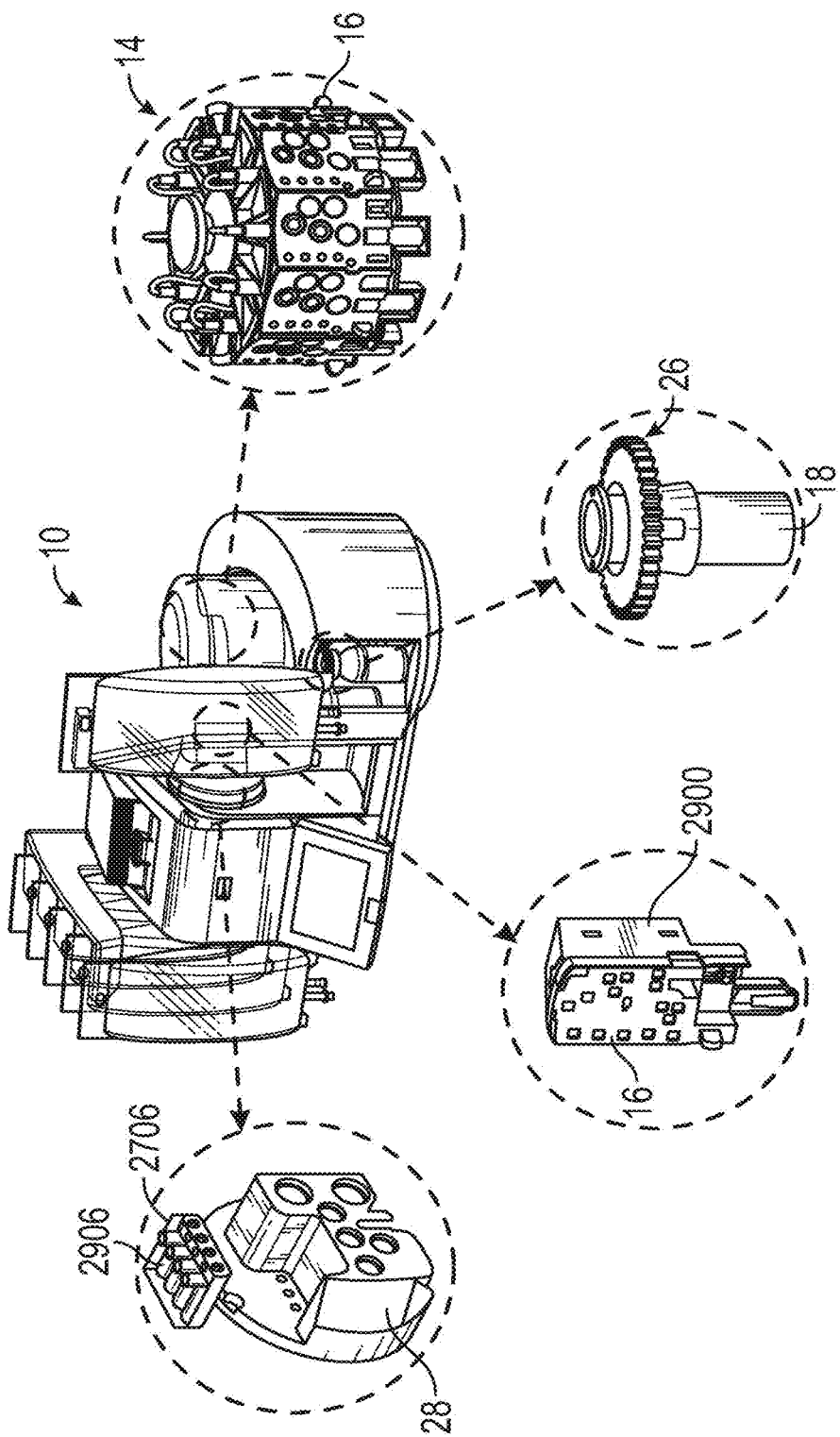
FIG. 29 illustrates a perspective view of the compounding system of FIG. 24 with various components shown in enlarged views for clarity in accordance with aspects of the present disclosure.

FIG. 29 shows another perspective view of compounder 10 highlighting the locations of various particular components such as the carousel 14 with cartridges 16 mounted therein, a cartridge 16 having a backpack 2900, a vial puck 26 for mounting vials 18, and pump head assembly 28 with a diluent magazine 2706 containing a plurality of manifolds 2906 in accordance with an embodiment. Further features of the diluent magazine 2904 and manifolds 2906 will be described hereinafter in connection with FIGS. 30-50.

Figure 30:
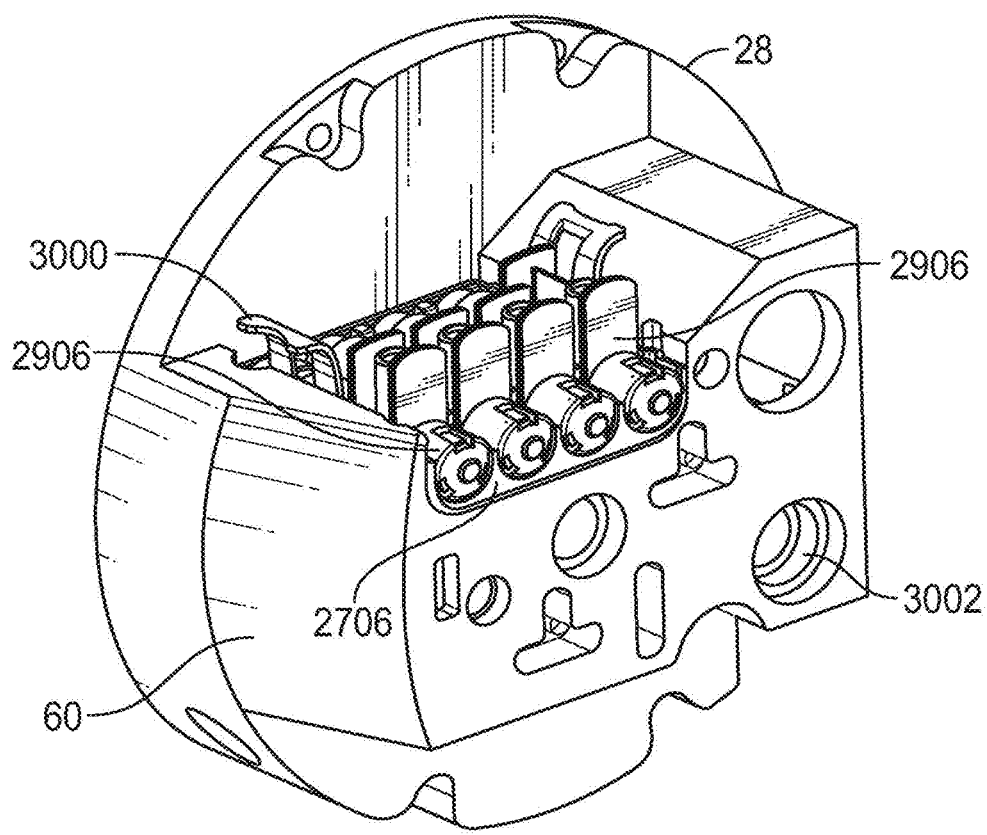
FIG. 30 illustrates a perspective view of a magazine having a plurality of manifolds disposed in a magazine recess of a pump head assembly in accordance with aspects of the present disclosure.

Turning now to FIG. 30, pump head assembly 28 is shown according to an embodiment. As shown in FIG. 30, a plurality of manifolds 2906 may be disposed in a magazine 2706 that is shaped and sized to be received in the slot 60 of the pump head assembly. Magazine 2706 may include a pair of extended wings 3000 that are squeezable by a user to remove and install the magazine in the slot. In the example of FIG. 30, a plurality of openings 3002 are also shown in the pump head assembly through which various other pump control components such as components 2708 of FIG. 27 can extend to operate other portions of compounder system 10 (e.g., to controllably pump fluid through a cartridge 16).

Figure 31:
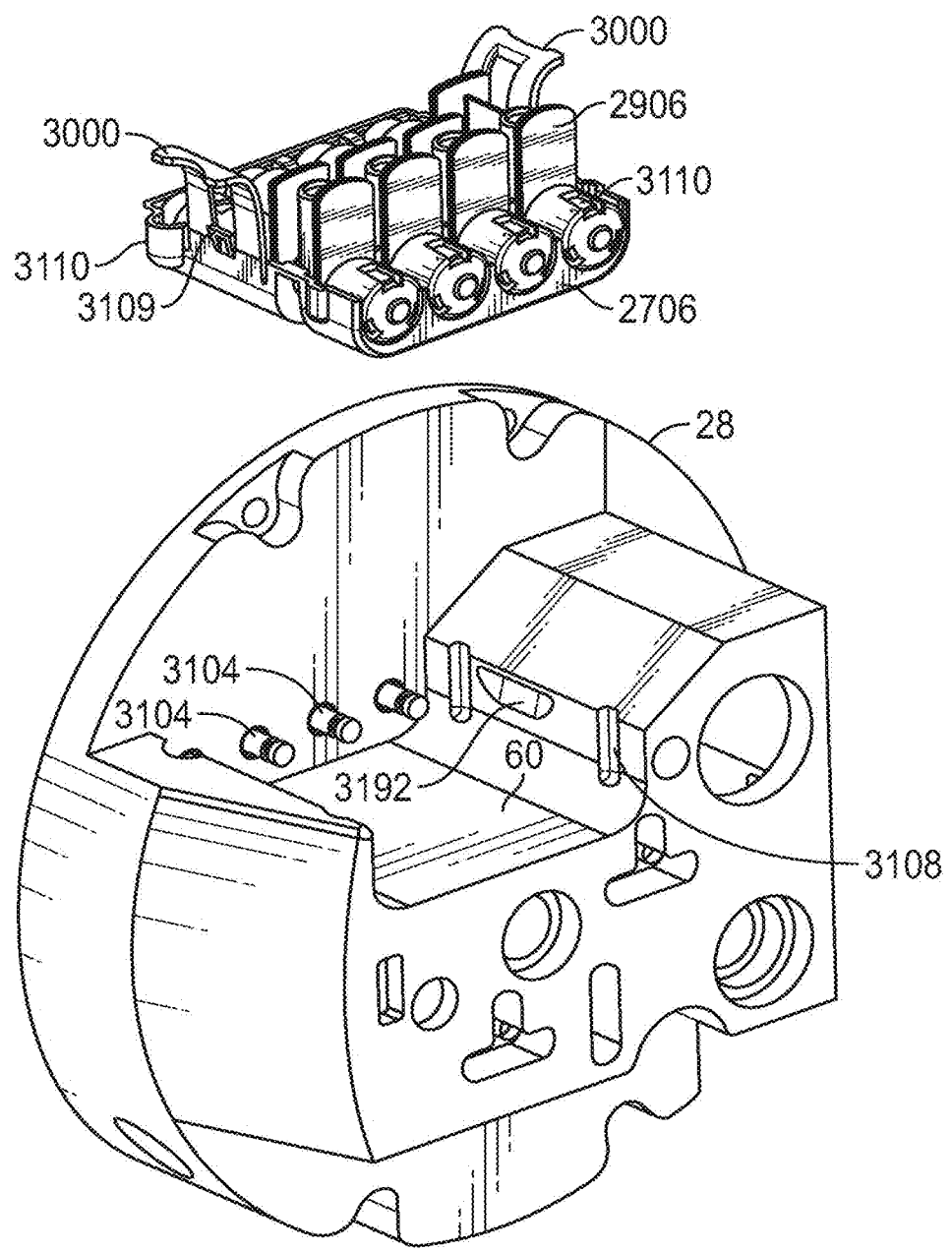
FIG. 31 illustrates an exploded perspective view of the magazine and pump head assembly of FIG. 30 in accordance with aspects of the present disclosure.

FIG. 31 is an exploded view of the assembly of FIG. 30 in which a plurality of needle push rods 3104 can be seen extended from pump head assembly 28 into the slot 60. Each needle push rod 3104 may be extended and/or retracted by the pump drive assembly to actuate a needle assembly in a corresponding manifold 2906. Magazine 2706 may include one or more alignment features 3110 each having a shape, size, and position that corresponds to associated alignment features 3108 in slot 60 that guide magazine 2706 into the slot and prevent incorrect insertion of the magazine in the slot (e.g., by providing a mechanical barrier to insertion if the magazine is in a reverse orientation). Alignment features 3110 may be protrusions on the body of the magazine that correspond to recesses 3108 in slot 60. However, this is merely illustrative and any combination of protrusions and/or recesses on magazine 2706 and slot 60 may be provided that guide magazine 2706 into the slot and prevent incorrect insertion of the magazine in the slot.

Magazine 2706 may include a snap feature 3109 configured to engage a corresponding snap feature 3106 in slot 60 to secure magazine 2706 in slot 60 during compounding operations. As illustrated, snap feature 3109 is implemented as a protrusion on the body of the magazine that corresponds to a recess 3106 in slot 60. However, this is merely illustrative. In other embodiments, snap features 3109 and 3106 may include a protrusion within slot 60 that corresponds to a recess in magazine 2706. As shown in FIG. 31, slot 60 may have a relatively smooth surface that can be easily wiped clean. When magazine 2706 is installed in slot 60, push rods 3104 may slide into corresponding slots in manifolds 2906 as will be discussed in further detail hereinafter.

Figure 32:
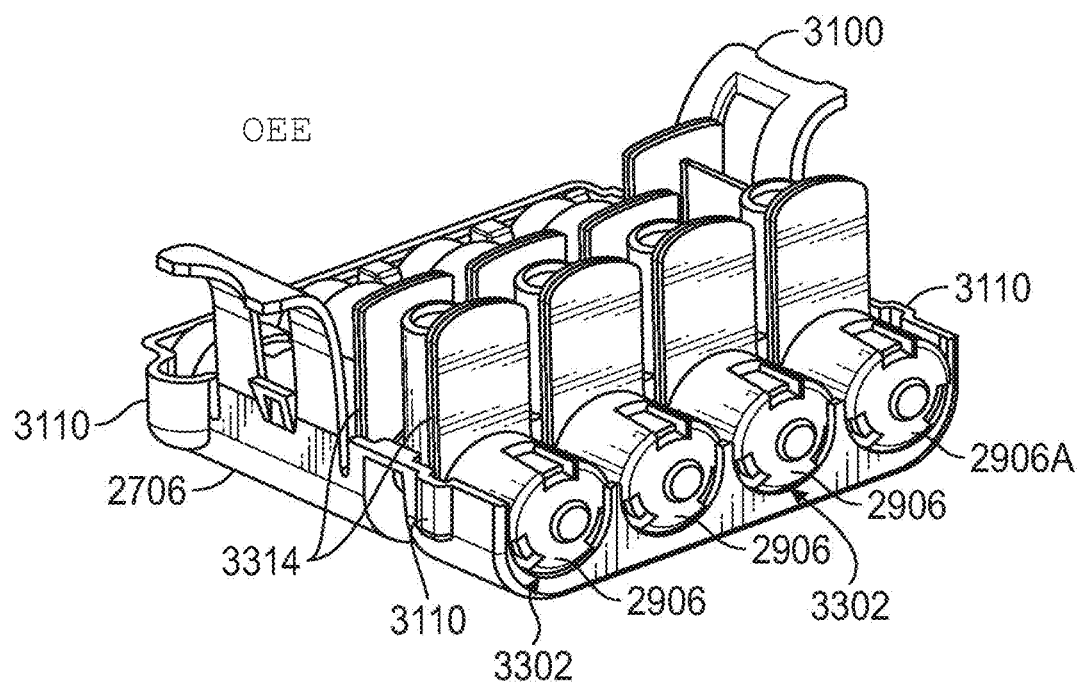
FIG. 32 illustrates a perspective view of a magazine having a plurality of manifolds in accordance with aspects of the present disclosure.

An enlarged perspective view of magazine 2706 and manifolds 2906 is shown in FIG. 32 in which it can be seen that magazine 2706 may be configured to hold, in one embodiment, three diluent manifolds 2906 and a waste manifold 2906A. As shown, waste manifold 2906A may have a different shape than the diluent manifolds to ensure that the waste manifold can only be installed at a particular position in the magazine. During compounding operations, a needle may be extended from a selected one of the diluent manifolds into a port in a pump cartridge to allow diluent from a corresponding container 42 to be pumped through cartridge to a vial 18 or to a receiving container 32. A needle may also be extended from waste manifold 2906A to a waste port in the pump cartridge to provide a sealed fluid path for vapor and/or liquid waste from the cartridge to a waste container 44.

Figure 33:
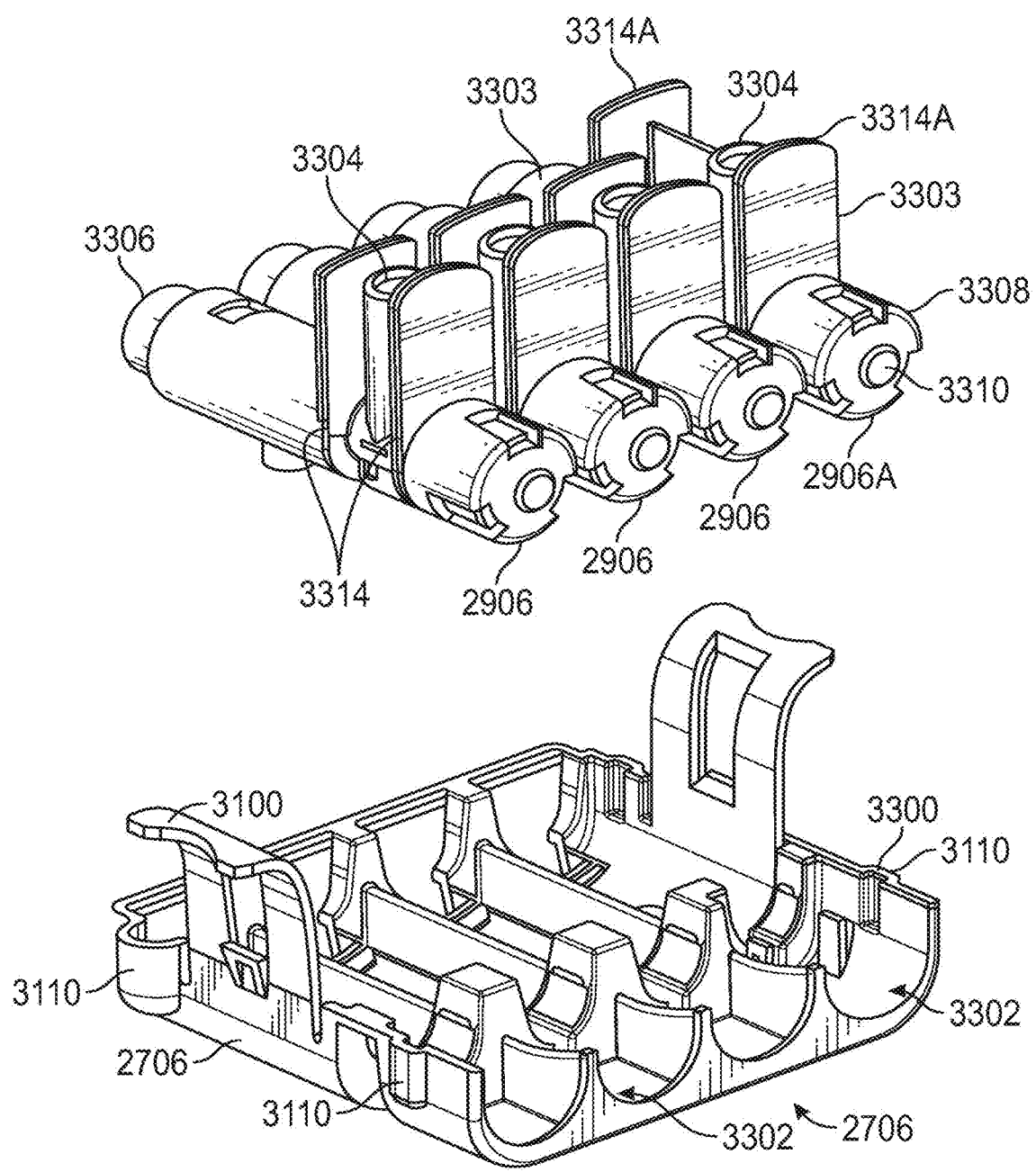
FIG. 33 illustrates an exploded perspective view of the magazine and manifolds of FIG. 32 in accordance with aspects of the present disclosure.

As shown in the exploded perspective view of FIG. 33, each manifold 2906 may include an opening 3304 configured to receive tubing that runs from the manifold to a corresponding diluent or waste container 42, 44. Each manifold 2906 may also include a cap assembly that includes a cap 3308 and a compressible membrane 3310 that extends through an opening in the cap to form a sealing member. The compressible membrane 3310 may be pressed against a membrane of the cartridge in the corresponding port of the cartridge and the needle may be extended through the membrane 3310 and the membrane of the cartridge to provide a sealed fluid pathway from containers 42 and 44 into an appropriate port in the cartridge for compounding operations.

Each manifold 2906 may include multiple components such as the cap assembly, a manifold housing 3303, and a needle guide assembly 3306. A needle assembly may be disposed within the needle guide assembly 3306 and the housing 3303 as will be described in further detail hereinafter. Each manifold 2906 may be placed into a corresponding recess 3302 on magazine 2706. As shown in FIG. 33, magazine housing 3300 may include alignment features within each recess 3302 that guide manifolds 2906 into the appropriate slot 3302. For example, each housing 3303 may include rails 3314 that slide over a corresponding alignment structure in a corresponding recess 3302 in magazine 2706. As shown, waste manifold 2906a may have rails 3314A that are spaced relatively further apart that the rails 3314 of the diluent manifolds to prevent the waste manifold from being installed in the magazine in the wrong position.

Figure 34:
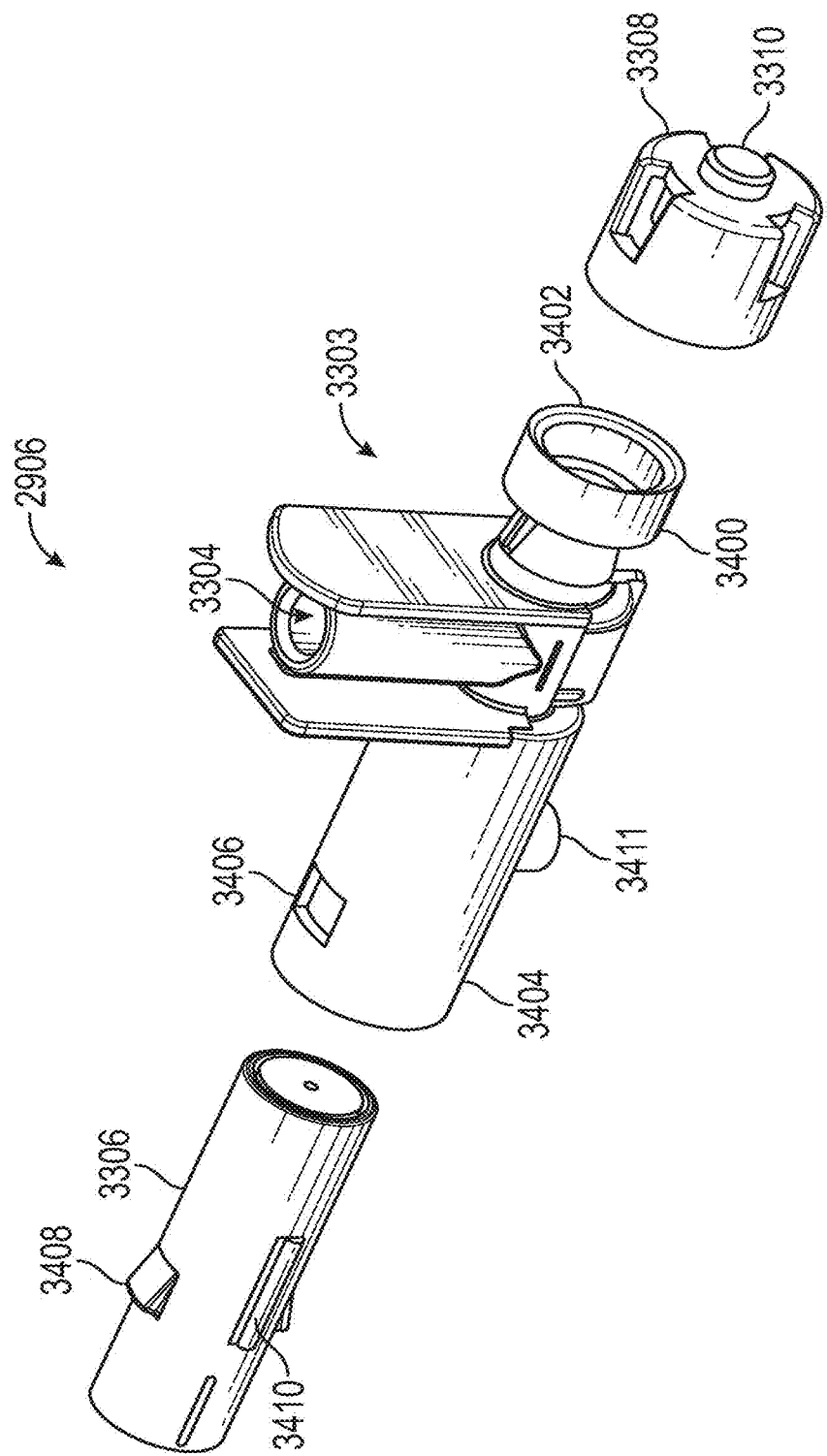
FIG. 34 illustrates an exploded perspective view of a manifold in accordance with aspects of the present disclosure.

FIG. 34 shows a partially exploded view of a manifold 2906 showing further details of the manifold housing 3303 and needle guide assembly 3306. As shown, needle guide 3306 may include guide ribs 3410 that align the needle guide assembly 3306 into a rear portion 3404 of housing 3303 until a snap feature 3408 engages in opening 3406 in the housing to secure the needle guide assembly in the housing.

Figure 35:
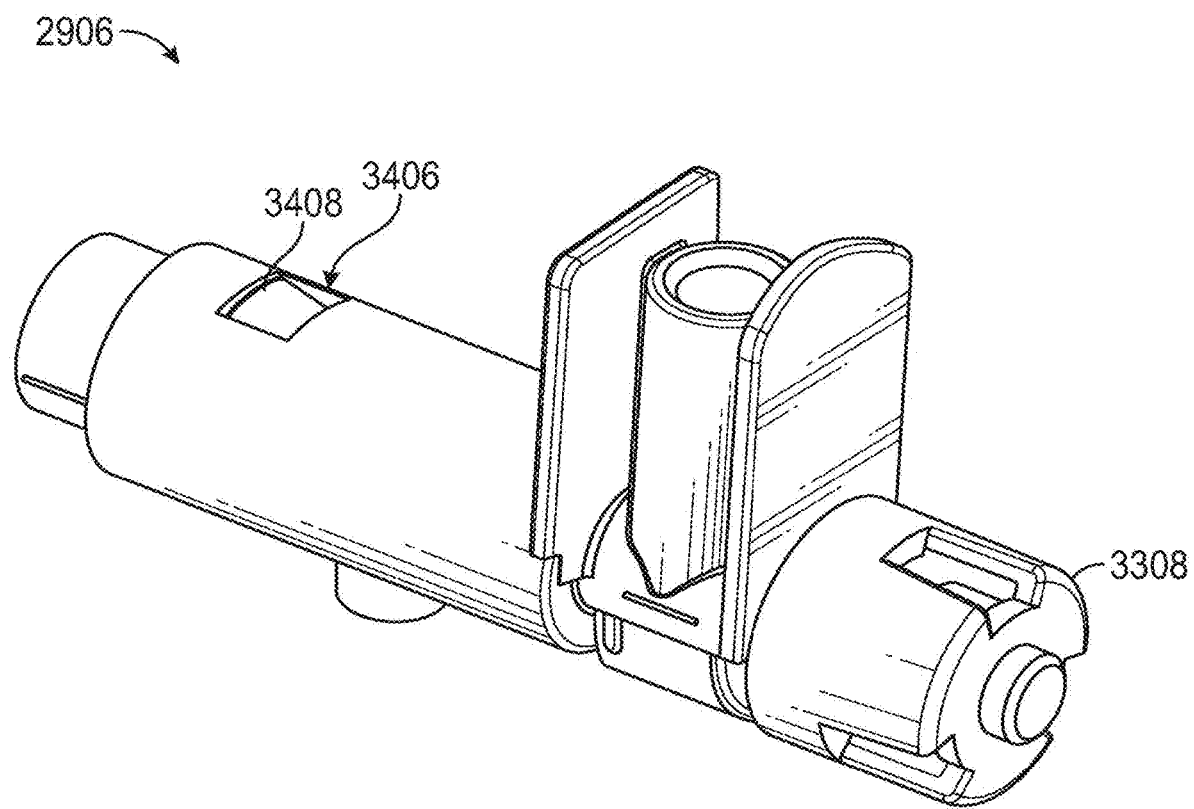
FIG. 35 illustrates a perspective view of an assembled manifold in accordance with aspects of the present disclosure.

Housing 3303 may include one or more alignment features such as protrusion 3411 that help align and secure the manifold in the magazine. Housing 3303 may also include a cap mount portion 3400. Cap 3308 may be configured to snap onto cap mount portion 3400 to secure cap 3308 onto housing 3303 such that a fluid pathway 3402 is sealed by membrane 3310. Fluid pathway 3402 may be fluidly coupled to opening 3304. FIG. 35 shows an assembled perspective view of manifold 2906 with cap 3308 disposed on cap mount portion 3400 and with snap feature 3408 disposed in opening 3406.

Figure 36:
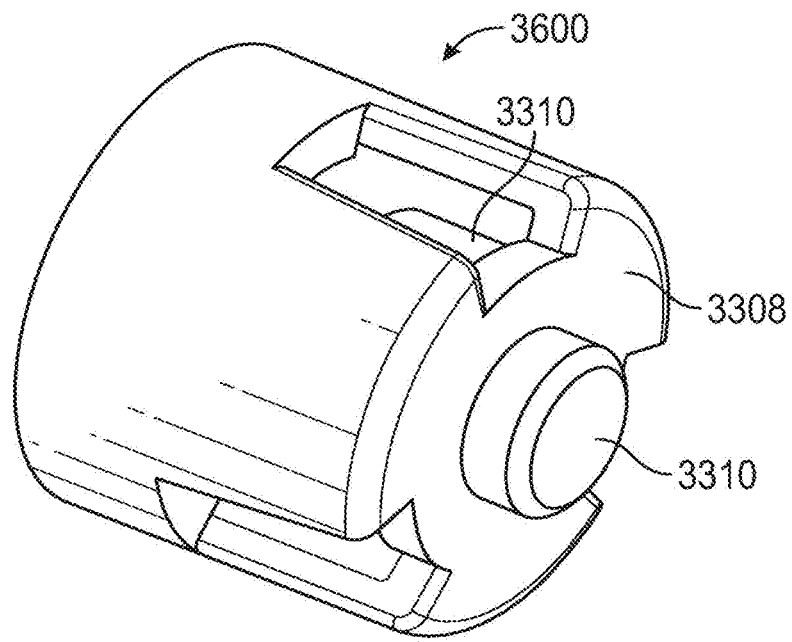
FIG. 36 illustrates a perspective view of a manifold cap assembly in accordance with aspects of the present disclosure.
Figure 37:
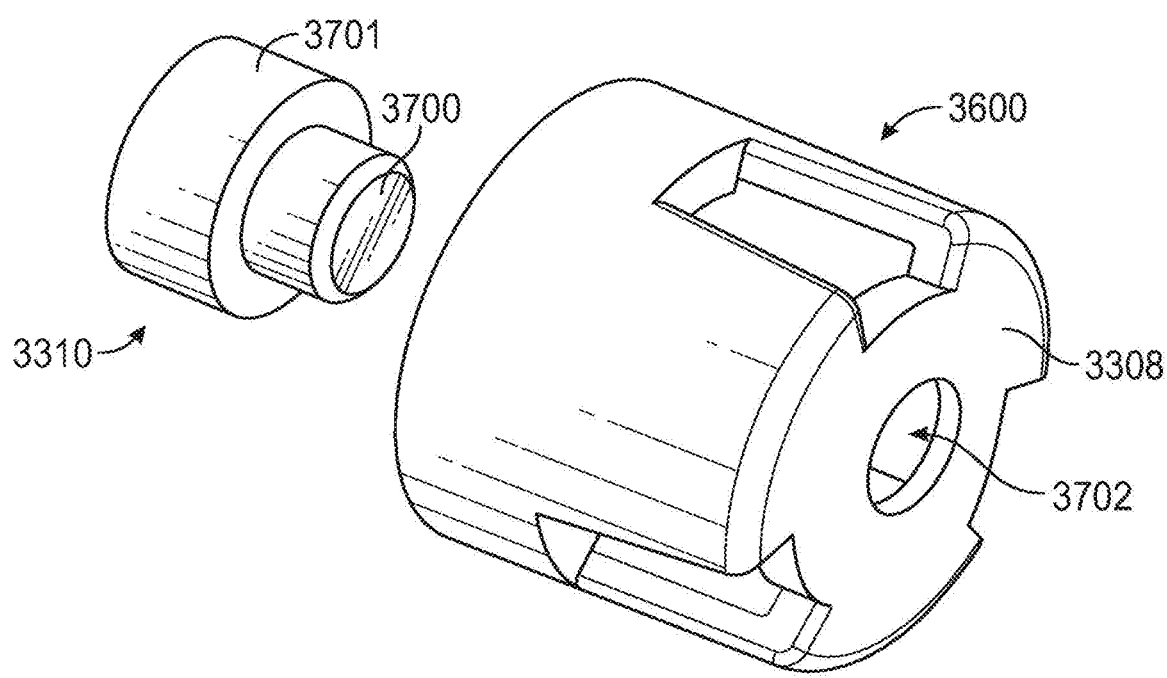
FIG. 37 illustrates an exploded perspective view of a manifold cap assembly in accordance with aspects of the present disclosure.
Figure 38:
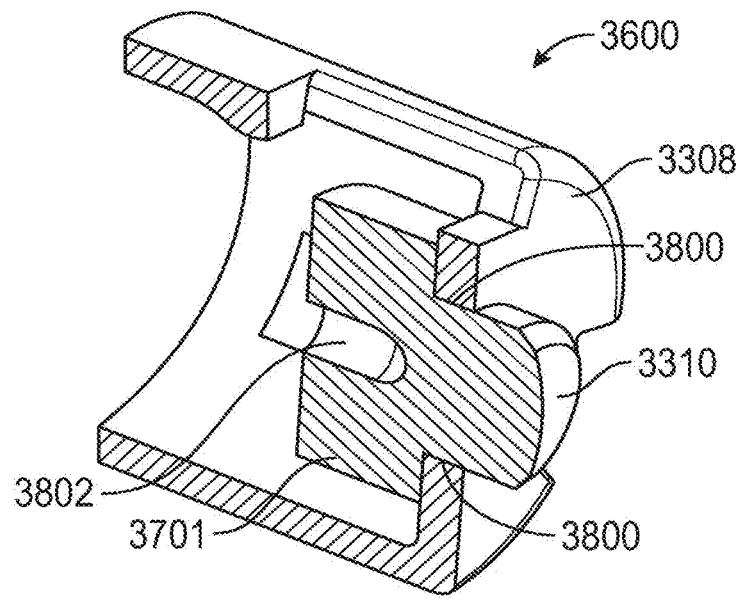
FIG. 38 illustrates a cross-sectional perspective view of a manifold cap assembly in accordance with aspects of the present disclosure.

Further details of cap assembly 3600 are shown in FIGS. 36-38. FIG. 36 shows a perspective view of cap assembly 3600 showing how membrane 3310 may be located within cap 3308 such that a portion of the membrane 3310 protrudes through an opening in cap 3308. The opening 3702 in cap 3308 is shown in FIG. 37. As shown in FIG. 37 membrane 3310 may include a base portion 3701 and a protruding portion 3700 that form a sealing member for cap assembly 3600. Opening 3702 in cap 3308 may have a diameter that is smaller than the diameter of protruding portion 3700 so that protruding portion 3700 is compressed (e.g., by 10 percent radially) by an edge of opening 3702 when membrane 3701 is pressed into cap 3308. By compressing protruding portion 3700, a needle that passes through membrane 3310 to allow fluid to flow through membrane 3310 may be wiped by membrane 3310 when the needle is retracted from the membrane 3310. In this way, manifold 2906 may provide a drip-free, sealed coupling between diluent and/or waste containers 42 and 44 and cartridge 16 when needed.

FIG. 38 is a cross-sectional view of cap assembly 3600 showing how contact points 3800 between cap 3308 and compressible membrane 3310 can bear against membrane 3310 to radially compress the membrane. As shown in FIG. 38 base portion 3701 may include a recess 3802 for receiving the tip of a needle of the manifold as will be discussed in further detail hereinafter.

Figure 39:
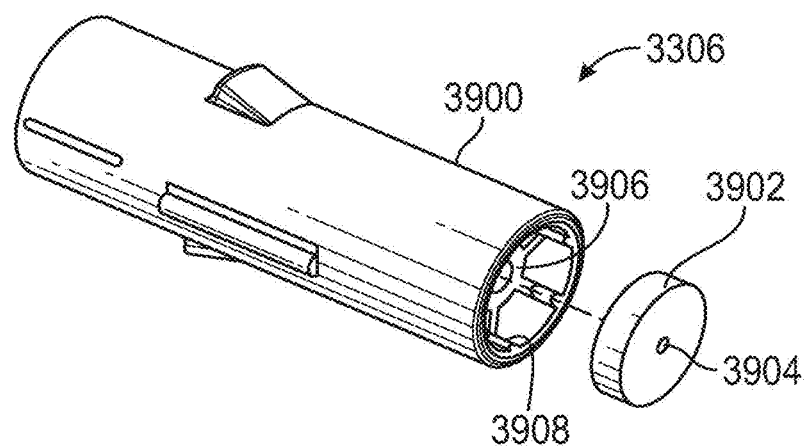
FIG. 39 illustrates an exploded perspective view of a manifold needle guide assembly in accordance with aspects of the present disclosure.
Figure 40:
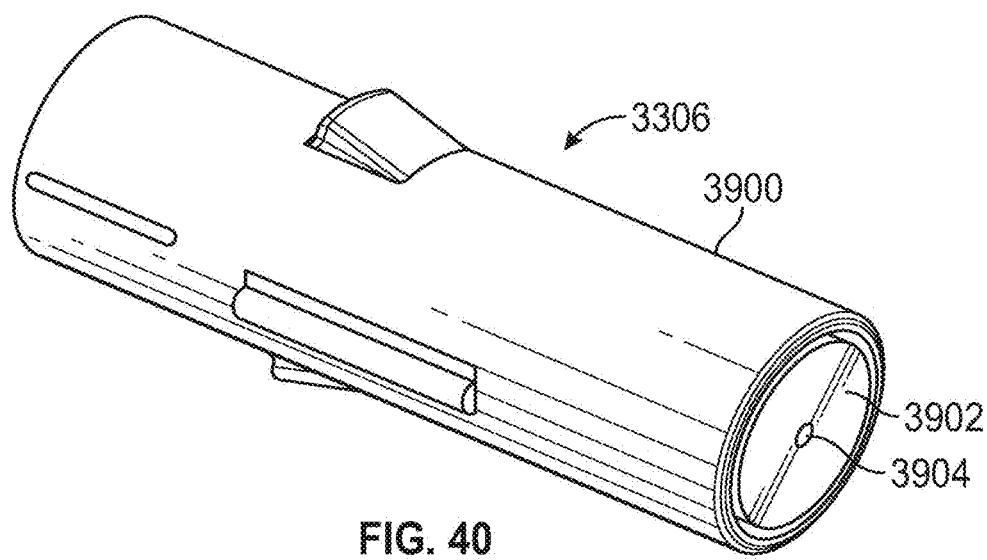
FIG. 40 illustrates an assembled perspective view of a manifold cap assembly in accordance with aspects of the present disclosure.
Figure 41:
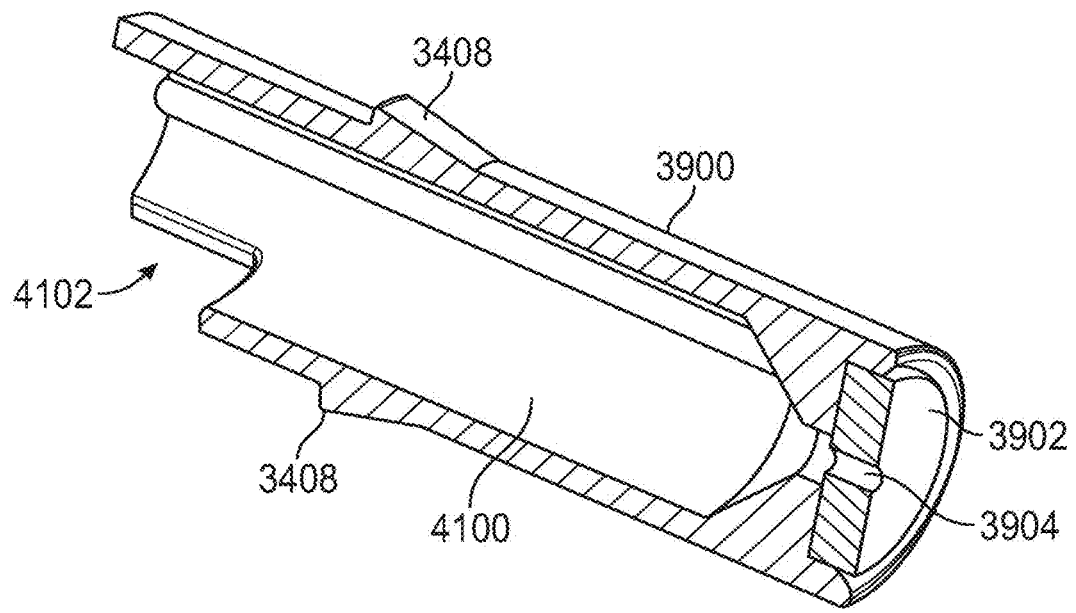
FIG. 41 illustrates a cross-sectional perspective view of a manifold cap assembly in accordance with aspects of the present disclosure.

Further details of needle guide assembly 3306 are shown in FIGS. 39-41. FIG. 39 shows an exploded perspective view of assembly 3306 showing how assembly 3306 may include an inner housing member 3900 and an inner seal member 3902. Inner seal member 3902 may include an opening 3904 configured to receive a needle. As shown, inner housing 3900 may include a mounting structure 3906 including a plurality of ribs 3908 configured to hold inner seal 3902 within inner housing 3900. FIG. 40 shows an assembled view of needle guide assembly 3306.

FIG. 41 shows a cross-sectional view of needle guide assembly 3306 showing how inner housing 3900 may include an internal bore 4100 that is fluidly connected to opening 3904. Inner bore 4100 and opening 3904 may cooperate to guide a needle assembly having a needle that extends through opening 3904. Inner housing 3900 may include a cutout 4102 on a bottom rear side that accommodates access of a needle push rod to the needle assembly.

Figure 42:
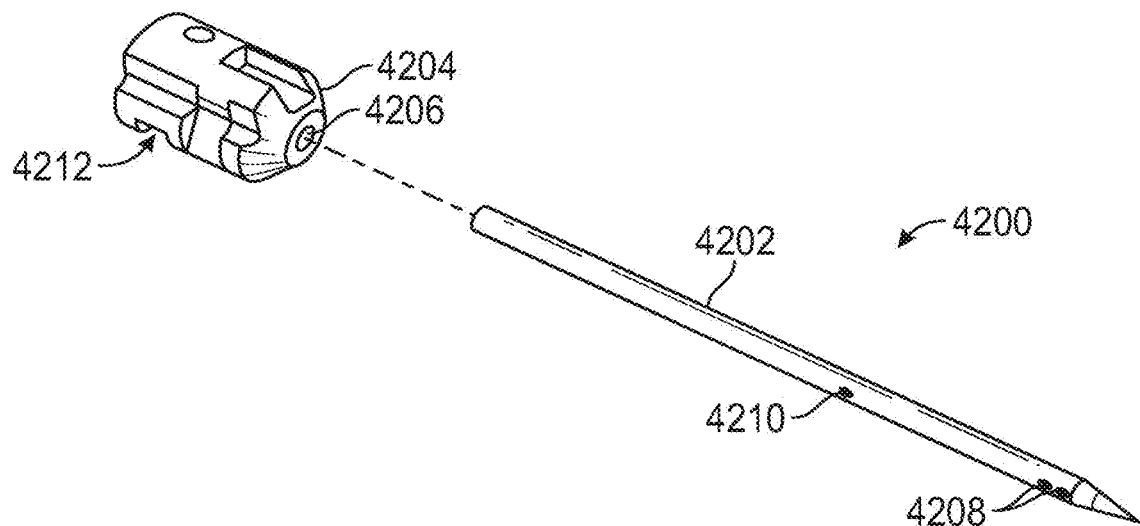
FIG. 42 illustrates an exploded perspective view of a manifold needle assembly in accordance with aspects of the present disclosure.
Figure 43:
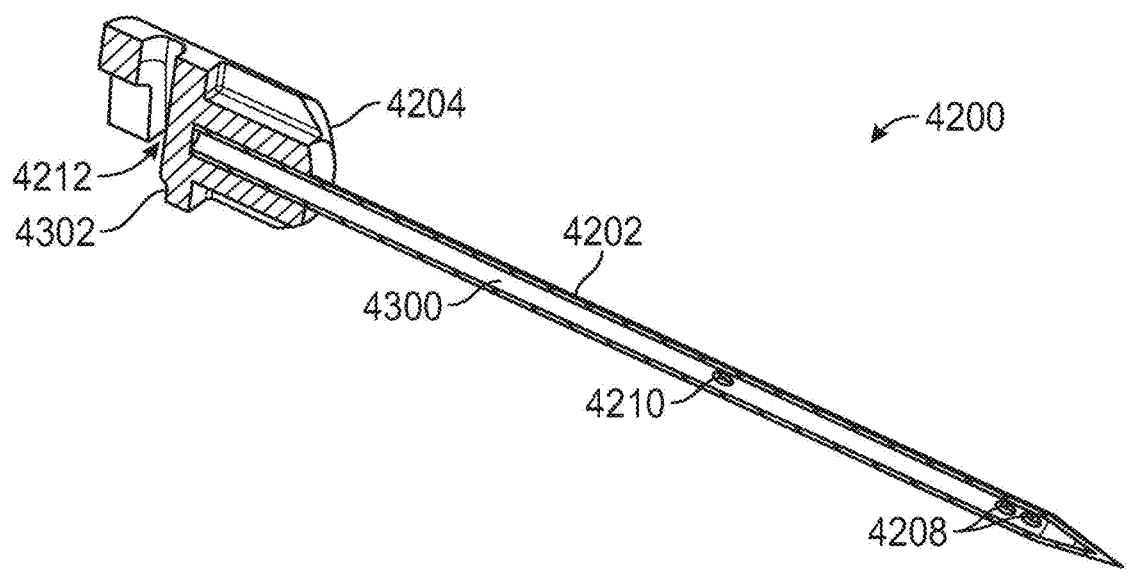
FIG. 43 illustrates a cross-sectional perspective view of a manifold needle assembly in accordance with aspects of the present disclosure.

FIGS. 42 and 43 show a needle assembly that may be at least partially disposed within needle guide assembly 3306. As shown in FIG. 42, needle assembly 4200 may include a needle 4202 and a needle housing 4204. Needle housing 4204 may be insert molded onto the needle in some embodiments. As shown, needle 4202 may include openings such as forward openings 4208 disposed proximal to the tip of the needle and one or more rear openings such as opening 4210.

Needle housing 4204 may include an opening 4206 for receiving a rear end of needle 4202 and a slot 4212. Slot 4212 may be configured to receive one of needle push rods 3104 (FIG. 31) when a magazine with the manifold is inserted in slot 60 of pump head assembly 28.

FIG. 43 is a cross sectional view of needle assembly 4200 showing how needle 4202 may include a central bore 4300. Openings 4208 and 4210 may be arranged to allow fluid to flow through bore 4300 of needle 4202. Needle housing 4204 may include a base member 4302 that bears against a rear end of needle 4202. A push rod disposed in slot 4202 may push and pull needle 4202 via needle housing 4204 such that the needle assembly is guided within needle guide assembly 3306 when the push rod is actuated to actuate the needle.

Figure 44:
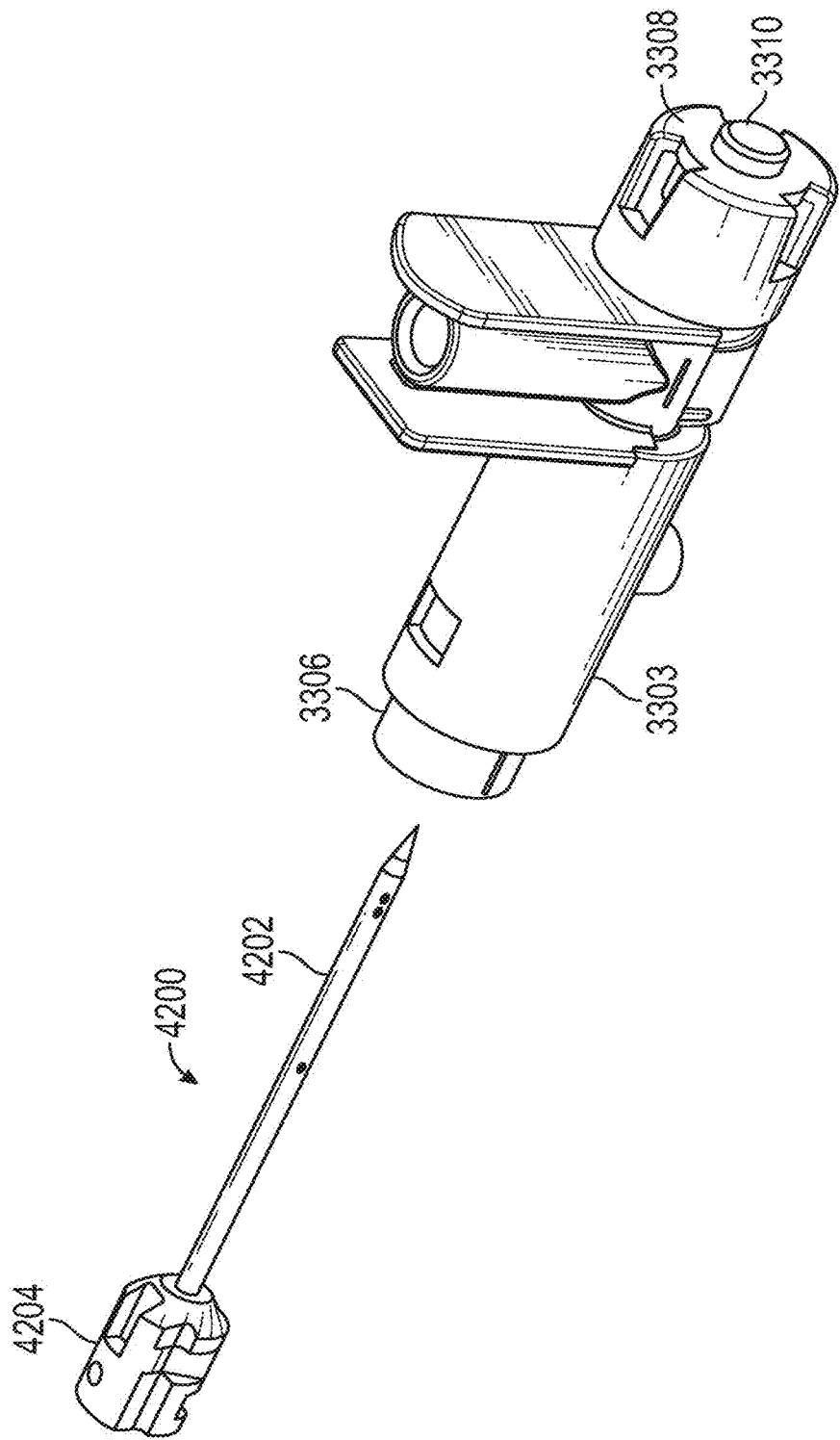
FIG. 44 illustrates a partially exploded perspective view of a manifold in accordance with aspects of the present disclosure.
Figure 45:
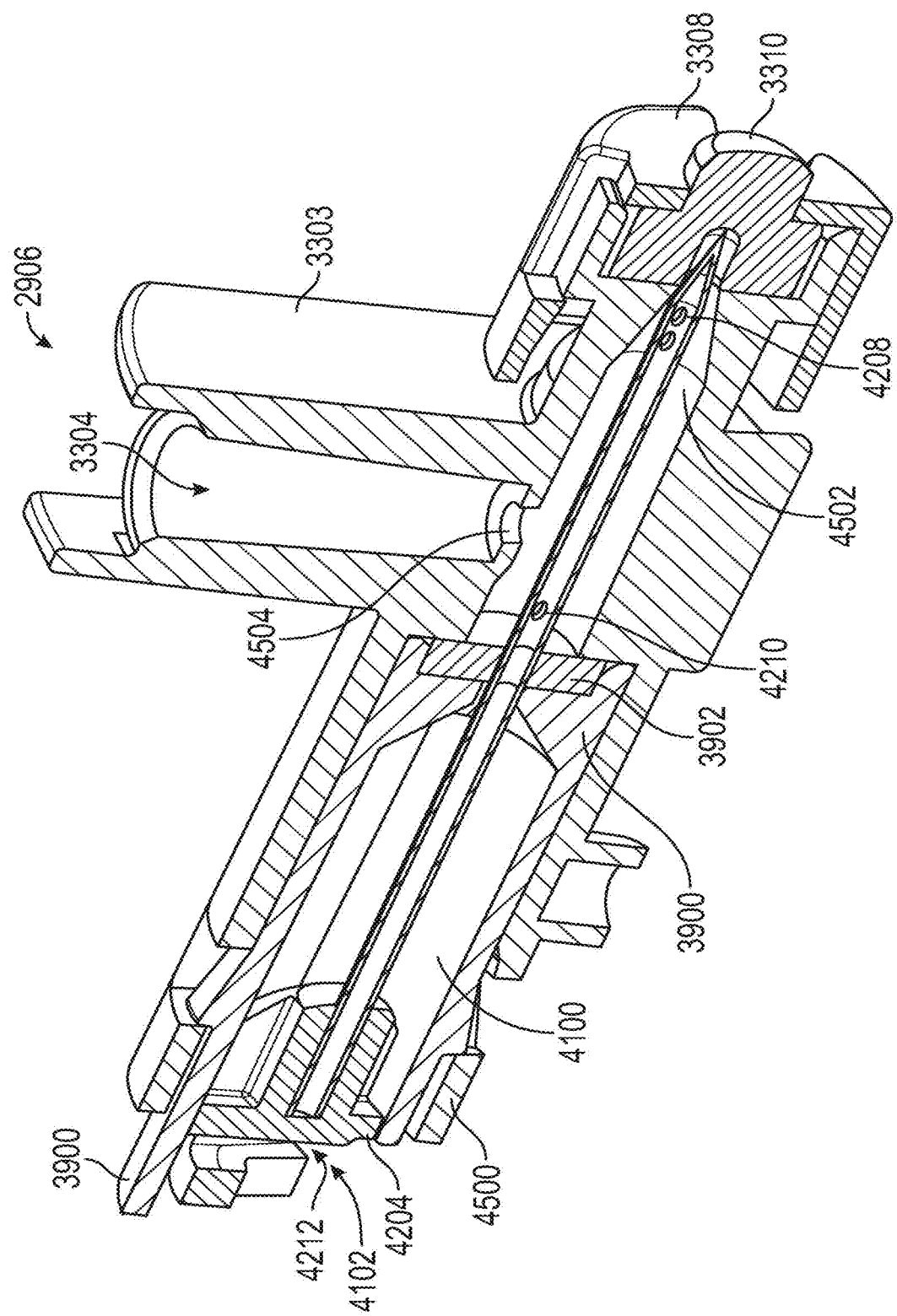
FIG. 45 illustrates a cross-sectional perspective view of a manifold in accordance with aspects of the present disclosure.

FIG. 44 is a partially exploded perspective view of manifold 2906 with needle assembly 4200 aligned for insertion into needle guide assembly 3306. FIG. 45 is a cross-sectional perspective view of manifold 2906 with needle assembly 4200 disposed therein. As shown in FIG. 45, needle housing 4204 may be located within central bore 4100 of inner housing and needle 4202 may extend from needle housing 3204 through central bore 4100 and through the opening in sealing member 3902 into a coaligned bore 4502 in manifold housing 3303.

Slot 4212 of needle housing 4204 may be disposed over cutout 4102 so that a needle push rod may be seated in slot 4212 for actuating needle 4202 through membrane 3310 to form a closed fluid path via needle 4202 (e.g., via openings 4208 and 4210 and central bore 4300) through membrane 3310. Slot 4212 may be formed in a portion of inner housing 3900 that extends from a beyond a rear portion 4500 of manifold housing 3303.

Manifold housing 3303 may include an opening 4504 between bore 4502 and opening 3304. In the configuration shown in FIG. 45, inner seal 3902 and membrane 3310 prevent any fluid from flowing to or from opening 3304 via bore 4502. However, if needle 4202 is actuated forward such that openings 4208 and 4210 are disposed on opposing sides of membrane 3310, then bore 4300 of needle 4202 forms a closed fluid pathway from opening 3304 (e.g., from a diluent container coupled by tubing to opening 3304) through needle 4202 and through membrane 3310 (e.g., into a pump cartridge 16).

Figure 46:
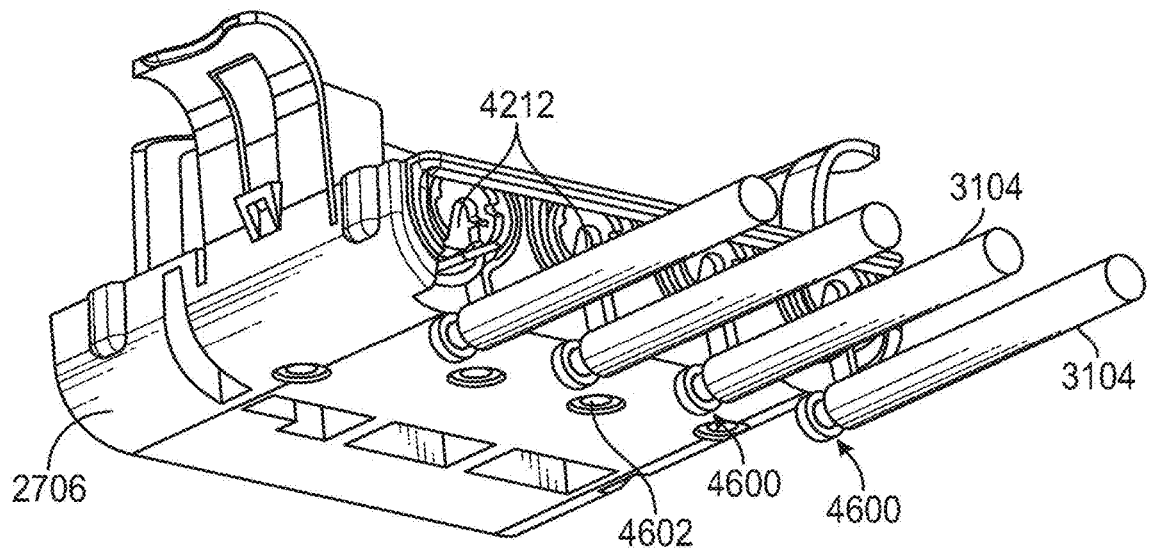
FIG. 46 illustrates a perspective bottom view of a magazine disposed above a plurality of manifold needle push rods in accordance with aspects of the present disclosure.
Figure 47:
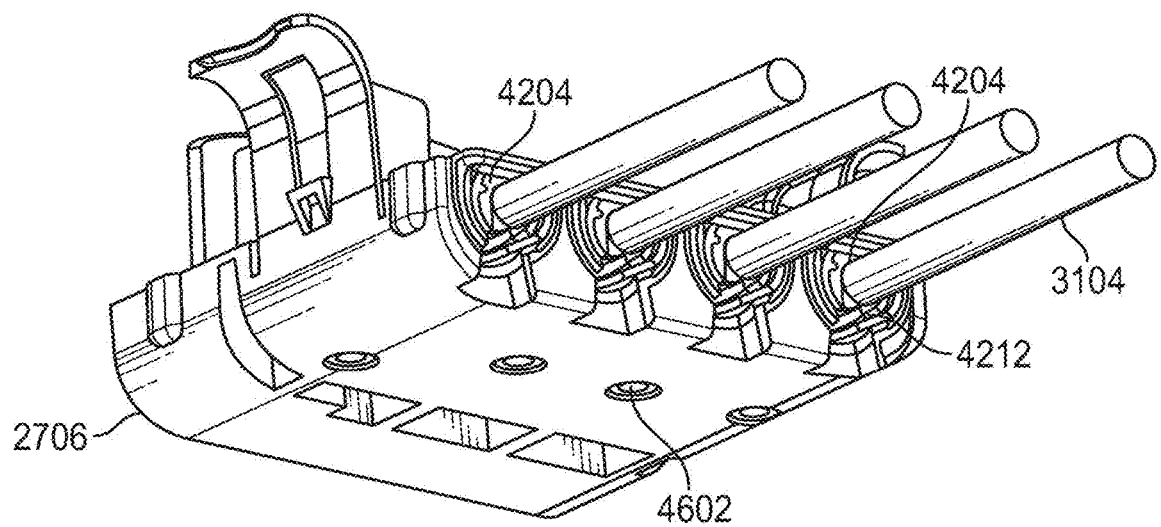
FIG. 47 illustrates a bottom perspective view of a magazine with a plurality of needle push rods disposed in rod recesses in a corresponding plurality of manifolds in the magazine in accordance with aspects of the present disclosure.

FIG. 46 is a bottom perspective view of magazine 2706 in which a plurality of manifolds 2906 are mounted. As shown in FIG. 46, each needle push rod 3104 may include an engagement feature 4600 configured to engage in slot 4212 of a corresponding manifold 2906. Guide openings 4602 may also be formed in a bottom surface of magazine 2706 that receive protrusions 3411 of manifold housing to help guide manifolds 2906 into the appropriate position in the appropriate recess in magazine 2706 and also help ensure that the manifolds remain upright in the recess. FIG. 47 shows needle push rods 3104 each engaged with a needle housing 4204 of a corresponding manifold. Pump drive assembly 20 may be configured to actuate one or more push rods 3104 to actuate a corresponding needle in a corresponding manifold.

Because needle 4202 can be extended through membrane 3310 or retracted to seal membrane 3310, each manifold 2906 can have a disengaged position and an engaged position. In the disengaged position, needle 4202 is completely contained within manifold 2906 and fluid is prevented from flowing through manifold 2906. In the engaged position, needle 4202 is extended through membrane 3310 with openings on opposing sides of membrane 3310 that allow fluid to flow through the central bore of the needle and thus through the manifold. In this way, a drip-free manifold may be provided to selectively allow fluid to flow (e.g., from a diluent container to a pump cartridge or from a pump cartridge to a waste container).

Figure 48:
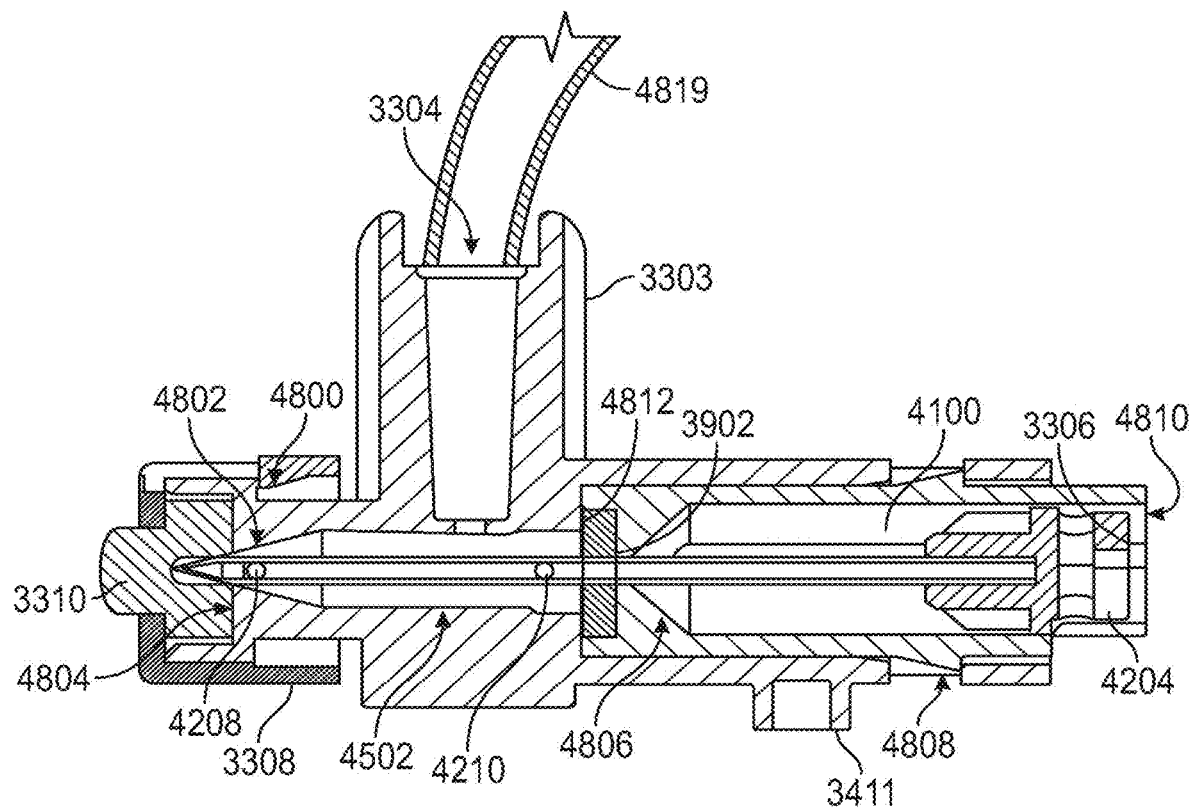
FIG. 48 illustrates a cross-sectional view of a manifold in a disengaged configuration in accordance with aspects of the present disclosure.

FIG. 48 is a cross-sectional view of manifold 2906 in the disengaged position. As shown in FIG. 48, in the disengaged position, both openings 4208 and 4210 of needle 4202 are located within bore 4502 of manifold housing 3303 and membrane 3310 is sealed. Thus, in the disengaged position, fluid from tubing 4819 (e.g., tubing such as tubing 50 that is fluidly coupled to outlet port 36 of a diluent container) is prevented from flowing through manifold 2906. Similarly, in the disengaged position, fluid and vapor are prevented from flowing into manifold 2906 through membrane 3310.

As shown in FIG. 48, central bore 4100 and coaligned bore 4502 may each have a ramped surface at a forward end that forms a needle guide (see needle guides 4806 and 4802 respectively) that ensure proper positioning of needle 4202 when the needle assembly is inserted into manifold 2906. As shown, manifold housing 3303 and membrane 3310 may form a seal 4804 that prevents fluid or vapors from flowing around membrane 3310 into or out of manifold 2906 at the forward end. Similarly, manifold housing 3303 and sealing member 3902 may form a seal 4812 that prevents fluid or vapors from flowing around member 3902 into or out of manifold 2906 at the rear end (e.g., between housing 3303 and internal bore 4100 of needle guide housing 3900). Guide ribs 4810 may also be provided on internal housing 3900 of needle guide assembly 3306 that guide needle housing 4204 within internal housing 3900. Snap features 4800 and 4808 that respectively secure cap 3308 and needle guide assembly 3306 within manifold housing 3303 are also shown in FIG. 48.

Figure 49:
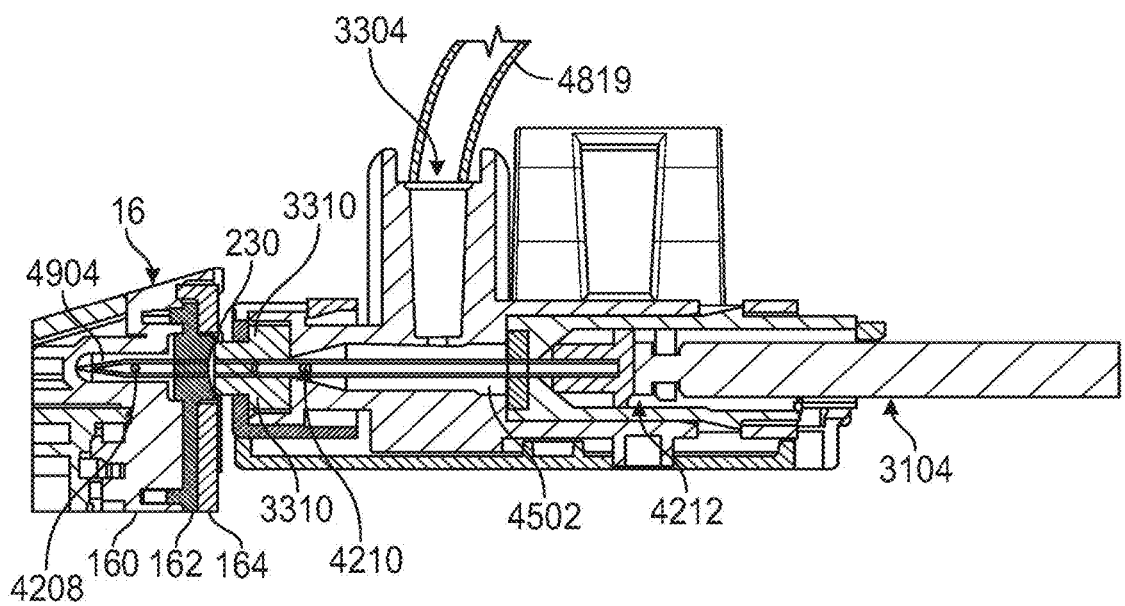
FIG. 49 illustrates a cross-sectional view of a manifold in an engaged configuration in accordance with aspects of the present disclosure.

FIG. 49 is a cross-sectional view of manifold 2906 in the engaged position. As shown in FIG. 49, in the engaged position, push rod 3104 has moved needle assembly 4200 forward such that needle 4202 has penetrated through membrane 3310 such that openings 4208 and 4210 of needle 4202 are disposed on opposing sides of membrane 3310. In this configuration, fluid can flow from tubing 4819 (e.g., from a diluent container) into opening 3304, through bore 4502, into needle 4202 through opening 4210 and out of opening 4208 into, for example, a pump cartridge 16. In other example, waste such as vapor waste or liquid waste from a compounding operation can flow from cartridge 16 into needle 4202 through opening 4208, out of opening 4210 into bore 4502 and through opening 3304 into tubing 4819 to, for example, a waste container.

As shown in FIG. 49, a forward surface of membrane 3310 may be pressed against a compliant membrane 162 of cartridge 16 within opening 230 corresponding to a diluent port or waste port of the cartridge 16. Needle 4202 may be extended (e.g., using push rod 3104) through both membrane 3310 and membrane 162 to form a closed fluid path between manifold 2906 and a fluid pathway 4904 of cartridge 16.

In operation, a magazine having one or more manifolds such as three diluent manifolds and a waste manifold may be rotated by pump head assembly 28 to align with corresponding ports formed by openings 230 in a pump cartridge. A needle from a selected one of the diluent manifolds may be extended into the cartridge to provide a fluid path from a diluent container into the cartridge. The pump drive assembly may then operate a piston and/or one or more valves of the cartridge to pump the diluent into, for example a vial of a powdered or concentrated liquid drug to reconstitute the drug in the vial. The pump drive assembly may then operate the piston and one or more valves of the pump cartridge to pump the reconstituted drug into a receiving container.

A needle in the waste manifold may also be extended into the cartridge to provide a fluid path from a cartridge to a vapor and/or liquid waste container. The piston and one or more valves of the cartridge may also be operated to pump vapor and/or liquid waste from the pump cartridge, through the waste manifold, and into a waste container. After the appropriate amount of a drug has been provided into the receiving container, the needles of the manifolds may be retracted using the push rods into the respective manifolds. As the needles are retracted, the sealing members of the cartridge and the manifold may effectively wipe the needle of any liquid so that, when the cartridge and the manifold are separated, no liquid waste is formed outside of the closed system of the cartridge or the closed system of the manifold.

Manifolds for the diluent and waste containers may be provided in an integrated assembly with the corresponding diluent and waste containers. Membrane 3310 of a manifold 2906 may have a resiliency that allows the membrane to be pierced by a manifold needle multiple times (e.g., up to 50 times) without compromising the seal formed by the membrane 3310 when the needle is retracted into the manifold. In this way, a diluent container or waste container can be used for compounding with multiple cartridges, with drugs from multiple vials and/or into multiple containers.

Figure 50:
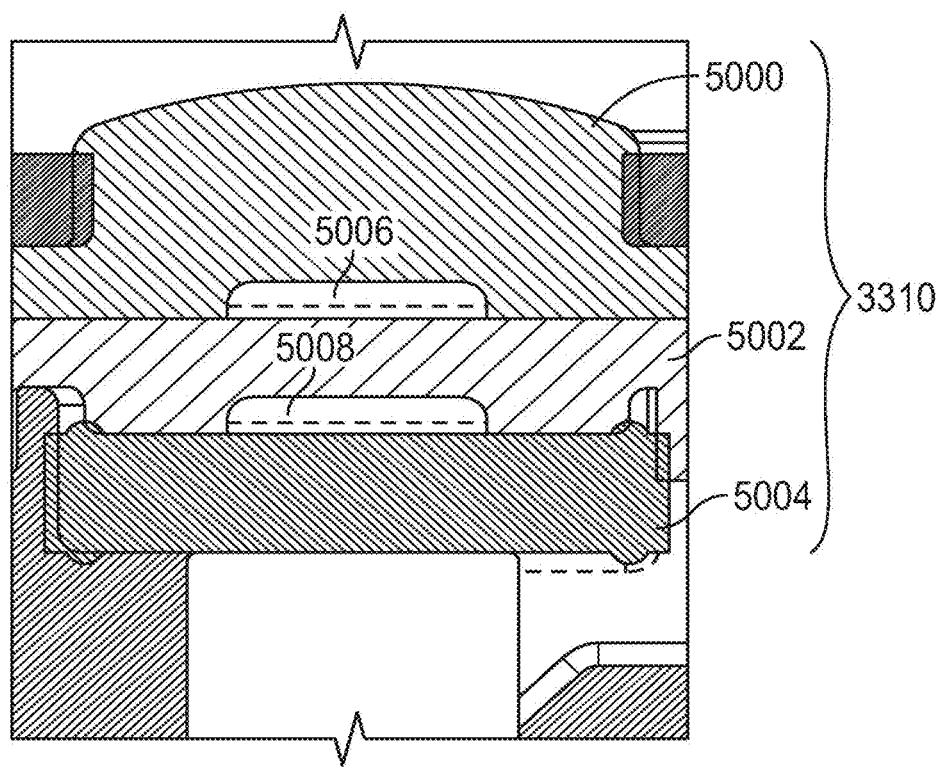
FIG. 50 illustrates a cross-sectional side view of a portion of a manifold having multiple sealing members in accordance with aspects of the present disclosure.

FIG. 50 shows a cross-sectional view of a portion of manifold 2906 in an implementation with three sealing members. As shown in FIG. 50, sealing member 3310 may be formed from an outer sealing member 5000, an intermediate sealing member 5002, and an inner sealing member 5004. Intermediate sealing member 5002 may be disposed between outer sealing member 5000 and an inner sealing member 5004.

As shown in FIG. 50, outer sealing member 5000 may, similarly to sealing member 3310 in FIG. 38 (for example), include a portion that extends through an opening within cap 3308 of manifold 2906. The central opening in which outer sealing member 5000 is disposed may be smaller than sealing member 5000 so that sealing member 5000 is compressed by a surface of cap 3308 when installed in cap 3308 (e.g., radially compressed by up to or approximately 10% to provide a wiping effect on a needle that is inserted or removed from sealing member 5000).

Outer sealing member 5000 may include a recess 5006 in a surface adjacent to intermediate sealing member 5002. Intermediate sealing member 5002 may also include a recess 5208 on an interior surface adjacent to inner sealing member 5004. Providing multiple sealing members such as the three sealing members (i.e., member 5000, member 5002, and member 5004) may provide an enhanced wiping of needle 4202 to provide an improved dry disconnect in comparison with implementations with a single sealing member. However, this is merely illustrative. In various embodiments, one, two, three, or more than three sealing members for each manifold may be provided. Similarly, interstitial spaces formed from recesses 5006 and 5008 may further increase the efficiency of the wiping of needle 4202, however, in various embodiments, sealing members may be provided with or without recesses 5008 and/or 5008.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A manifold, comprising: a housing; a cap assembly having a first sealing member; a needle guide assembly having a second sealing member; and a needle assembly having a needle with a central bore, a first opening, and a second opening, wherein the needle assembly is extendible from a disengaged position in which the first and second openings are both disposed on a common side of the first sealing member between the first and second sealing members and an engaged position in which the first and second openings are disposed on opposing sides of the first sealing member.

Concept 2. The manifold of Concept 1 or any other Concept, wherein the housing comprises an opening configured to receive tubing from a container, and wherein, in the engaged position, the needle assembly is configured to allow flow of a liquid or a vapor through the opening in the housing, through the first and second openings in the needle, and through the central bore of the needle.

Concept 3. The manifold of Concept 2 or any other Concept, wherein the needle guide assembly comprises an inner housing having a central bore, and wherein the needle assembly comprises a needle housing configured to slide within the central bore of the inner housing.

Concept 4. The manifold of Concept 3 or any other Concept, wherein the needle housing comprises a slot configured to receive a needle push rod for actuating the needle assembly between the disengaged and engaged positions.

Concept 5. The manifold of Concept 4 or any other Concept, wherein the inner housing of the needle guide assembly comprises a cutout configured to provide access to the slot of the needle housing when the needle housing is in the disengaged position.

Concept 6. The manifold of Concept 5 or any other Concept, wherein the inner housing of the needle guide assembly comprises at least one snap feature configured to engage with the housing of the manifold to secure the needle guide assembly within the housing.

Concept 7. The manifold of Concept 2 or any other Concept, wherein the cap assembly further comprises a cap, wherein the first sealing member is disposed within the cap and wherein the cap is configured to snap onto the housing.

Concept 8. The manifold of Concept 7 or any other Concept, wherein the cap comprises an opening, wherein the first sealing member comprises a membrane having an extended portion, and wherein an edge of the opening in the cap bears against the extended portion of the first sealing member to radially compress the first sealing member.

Concept 9. The manifold of Concept 8 or any other Concept, wherein the extended portion of the first sealing member has a diameter and wherein the edge of the opening bears against the extended portion of the first sealing member to radially compress the first sealing member by approximately 10 percent of the diameter.

Concept 10. A compounder system, comprising: a pump head assembly having a recess and a plurality of operational mechanisms; a magazine configured to be received in the recess; a manifold configured to be received in the magazine; a container fluidly coupled to the manifold; and a pump cartridge configured to be operated by the plurality of operational mechanisms of the pump drive to pump a fluid from the container through the manifold into the pump cartridge, wherein the manifold comprises a needle assembly having a disengaged configuration in which the needle assembly is completely disposed within the manifold such that the manifold prevents flow of the fluid and an engaged configuration in which the needle of the needle assembly extends from the manifold into the pump cartridge such that the needle forms a portion of a sealed fluid pathway from the container to the pump cartridge.

Concept 11. The compounder system of Concept 10 or any other Concept, wherein the pump cartridge comprises: a frame having an opening; and a compliant membrane disposed adjacent the frame, wherein, in the engaged configuration, the needle extends through the opening in the frame and through the compliant membrane into the pump cartridge.

Concept 12. The compounder system of Concept 11 or any other Concept, wherein the manifold further comprises a cap assembly having a sealing member configured to be pressed against the compliant membrane of the pump cartridge, and wherein, in the engaged configuration, the needle extends through the sealing member of the cap assembly of the manifold and through the opening in the frame and through the compliant membrane into the pump cartridge.

Concept 13. The compounder system of Concept 10 or any other Concept, wherein the magazine comprises a plurality of recesses configured to receive a plurality of manifolds.

Concept 14. The compounder system of Concept 13 or any other Concept, wherein each recess comprises alignment features configured to guide a corresponding manifold into the recess and prevent incorrect installation of any manifold in the recess.

Concept 15. The compounder system of Concept 14 or any other Concept, wherein the plurality of recess comprises a plurality of diluent manifold recesses and at least one waste manifold recess, wherein the alignment features in the diluent manifold recesses are different from the alignment features in the waste manifold recess.

Concept 16. The compounder system of Concept 14 or any other Concept, wherein the magazine further comprises a pair of squeezable grips configured to facilitate installation and removal of the magazine from the recess of the pump head assembly.

Concept 17. A method, comprising: providing a plurality of manifolds in a magazine, each manifold fluidly coupled by tubing to a container; providing the magazine in a recess of a pump head assembly of a compounder system; aligning the plurality of manifolds with a corresponding plurality of ports in a pump cartridge; and extending a needle from at least one of the manifolds into the corresponding port in the pump cartridge to create a fluid pathway between the container that is fluidly coupled to that manifold and the pump cartridge.

Concept 18. The method of Concept 17 or any other Concept, wherein extending the needle comprises extending the needle through a sealing member of the manifold into the pump cartridge.

Concept 19. The method of Concept 18 or any other Concept, wherein providing the magazine in the recess comprises inserting the magazine into the recess such that a plurality of needle push rods of the pump head assembly are each engaged in a slot of a corresponding one of the manifolds, and wherein extending the needle comprises extending the needle using a selected one of the needle push rods.

Concept 20. The method of Concept 17 or any other Concept, wherein aligning the plurality of manifolds with the corresponding plurality of ports in the pump cartridge comprises: rotating the magazine with the pump head assembly; and removing the pump cartridge from a carousel of cartridges to a position adjacent the pump head assembly.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

One or more aspects or features of the subject matter described herein may be realized in digital electronic circuitry, integrated circuitry, specially designed ASICs (application specific integrated circuits), computer hardware, firmware, software, and/or combinations thereof. For example, infusion pump systems disclosed herein may include an electronic system with one or more processors embedded therein or coupled thereto. Such an electronic system may include various types of computer readable media and interfaces for various other types of computer readable media. Electronic system may include a bus, processing unit(s), a system memory, a read-only memory (ROM), a permanent storage device, an input device interface, an output device interface, and a network interface, for example.

Bus may collectively represent all system, peripheral, and chipset buses that communicatively connect the numerous internal devices of electronic system of an infusion pump system. For instance, bus may communicatively connect processing unit(s) with ROM, system memory, and permanent storage device. From these various memory units, processing unit(s) may retrieve instructions to execute and data to process in order to execute various processes. The processing unit(s) can be a single processor or a multi-core processor in different implementations.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. .sctn. 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. .sctn. 101, 102, or 103, nor should they be interpreted in such a way.

The invention claimed is:

1. A compounder system, comprising:
 a pump head assembly having a recess and a plurality of operational mechanisms;
 a magazine configured to be received in the recess;
 a manifold configured to be received in the magazine;
 a container fluidly coupled to the manifold; and
 a pump cartridge configured to be operated by the plurality of operational mechanisms of the pump drive to pump a fluid from the container through the manifold into the pump cartridge, wherein the manifold comprises a needle assembly having a disengaged configuration in which the needle assembly is completely disposed within the manifold such that the manifold prevents flow of the fluid and an engaged configuration in which a needle of the needle assembly extends from the manifold into the pump cartridge such that the needle forms a portion of a sealed fluid pathway from the container to the pump cartridge.

2. The compounder system of claim 1, wherein the pump cartridge comprises:
a frame having an opening; and
a compliant membrane disposed adjacent the frame,
wherein, in the engaged configuration, the needle extends through the opening in the frame and through the compliant membrane into the pump cartridge.

3. The compounder system of claim 2, wherein the manifold further comprises a cap assembly having a sealing member configured to be pressed against the compliant membrane of the pump cartridge.

4. The compounder system of claim 3, wherein, in the engaged configuration, the needle extends through the sealing member of the cap assembly of the manifold and through the opening in the frame and through the compliant membrane into the pump cartridge.

5. The compounder system of claim 1, wherein the magazine comprises a plurality of recesses configured to receive a plurality of manifolds.

6. The compounder system of claim 5, wherein each recess comprises alignment features configured to guide a corresponding manifold into the recess and prevent incorrect installation of any manifold in the recess.

7. The compounder system of claim 6, wherein the plurality of recess comprises a plurality of diluent manifold recesses and at least one waste manifold recess, wherein the alignment features in the diluent manifold recesses are different from the alignment features in the waste manifold recess.

8. The compounder system of claim 6, wherein the magazine further comprises a pair of squeezable grips configured to facilitate installation and removal of the magazine from the recess of the pump head assembly.

9. The compounder system of claim 1, wherein the manifold comprises:
a housing;
a cap assembly having a first sealing member; and
a needle guide assembly having a second sealing member, wherein the needle of the needle assembly has a central bore, a first opening, and a second opening.

10. The compounder system of claim 9, wherein the needle assembly is extendible from the disengaged position in which the first and second openings are both disposed on a common side of the first sealing member between the first and second sealing members and the engaged position in which the first and second openings are disposed on opposing sides of the first sealing member.

11. The compounder system of claim 9, wherein the housing comprises an opening configured to receive tubing from a container, and wherein, in the engaged position, the needle assembly is configured to allow flow of a liquid or a vapor through the opening in the housing, through the first and second openings in the needle, and through the central bore of the needle.

12. The compounder system of claim 9, wherein the needle guide assembly comprises an inner housing having a central bore, and wherein the needle assembly comprises a needle housing configured to slide within the central bore of the inner housing.

13. The compounder system of claim 12, wherein the needle housing comprises a slot configured to receive a needle push rod for actuating the needle assembly between the disengaged and engaged positions.

14. The compounder system of claim 13, wherein the inner housing of the needle guide assembly comprises a cutout configured to provide access to the slot of the needle housing when the needle housing is in the disengaged position.

15. The compounder system of claim 12, wherein the inner housing of the needle guide assembly comprises at least one snap feature configured to engage with the housing of the manifold to secure the needle guide assembly within the housing.

16. The compounder system of claim 9, wherein the cap assembly further comprises a cap, wherein the first sealing member is disposed within the cap and wherein the cap is configured to snap onto the housing.

17. The compounder system of claim 16, wherein the cap comprises an opening, wherein the first sealing member comprises a membrane having an extended portion, and wherein an edge of the opening in the cap bears against the extended portion of the first sealing member to radially compress the first sealing member.

18. The compounder system of claim 17, wherein the extended portion of the first sealing member has a diameter and wherein the edge of the opening bears against the extended portion of the first sealing member to radially compress the first sealing member by approximately 10 percent of the diameter.

19. The compounder system of claim 1, wherein the manifold comprises:
a housing; and
a cap assembly having a first sealing member and a cap, wherein the first sealing member is disposed within the cap and wherein the cap is configured to snap onto the housing.

20. The compounder system of claim 19, wherein the cap comprises an opening, wherein the first sealing member comprises a membrane having an extended portion, and wherein an edge of the opening in the cap bears against the extended portion of the first sealing member to radially compress the first sealing member.

* * * * *